(12) United States Patent
Hanberg et al.

(10) Patent No.: US 11,298,846 B1
(45) Date of Patent: Apr. 12, 2022

(54) CUTTING DEVICE FOR BRACHYTHERAPY SEED IMPLANTATION SLEEVES

(71) Applicant: Isoray Medical, Inc., Richland, WA (US)

(72) Inventors: Griffin Hanberg, Richland, WA (US); Donald Stefero, Richland, WA (US); Michael L Krachon, Atlanta, GA (US); Brian Berry, Lakeway, TX (US)

(73) Assignee: Isoray Medical, Inc., Richland, WA (US)

( * ) Notice: Subject to any disclaimer, the term of this patent is extended or adjusted under 35 U.S.C. 154(b) by 555 days.

(21) Appl. No.: 16/398,090

(22) Filed: Apr. 29, 2019

Related U.S. Application Data

(63) Continuation-in-part of application No. 16/165,178, filed on Oct. 19, 2018, now Pat. No. 10,328,278.

(60) Provisional application No. 62/580,837, filed on Nov. 2, 2017.

(51) Int. Cl.
| | |
|---|---|
| *B26D 3/16* | (2006.01) |
| *A61N 5/10* | (2006.01) |
| *B26D 1/08* | (2006.01) |
| *B26D 7/26* | (2006.01) |

(52) U.S. Cl.
CPC ............. *B26D 3/16* (2013.01); *A61N 5/1007* (2013.01); *B26D 1/08* (2013.01); *A61N 2005/101* (2013.01); *A61N 2005/1009* (2013.01); *A61N 2005/1024* (2013.01); *B26D 3/169* (2013.01); *B26D 7/2614* (2013.01)

(58) Field of Classification Search
CPC ............. A61N 5/107; B26D 3/16; B26D 1/08
See application file for complete search history.

(56) References Cited

U.S. PATENT DOCUMENTS

| | | | | |
|---|---|---|---|---|
| 4,972,749 | A * | 11/1990 | Grove | ..................... B27B 27/04 269/303 |
| 5,460,592 | A * | 10/1995 | Langton | ............... A61N 5/1027 600/7 |
| 2004/0186340 | A1* | 9/2004 | Reed | .................... A61N 5/1027 600/7 |
| 2016/0214268 | A1* | 7/2016 | Zaremski | ............. B26D 7/2628 |

* cited by examiner

*Primary Examiner* — John P Lacyk
(74) *Attorney, Agent, or Firm* — Etherton Law Group, LLC

(57) ABSTRACT

A device for loading brachytherapy seeds and spacers into a sleeve. The device holds two or more seed or spacer cartridges of different radioactive species and dosage. The user rotates a selector for selecting a desired cartridge and, with each depression of a spring-biased plunger, pushes a seed or spacer into a channel in an inspection area. The process is repeated for the desired number and order of seeds and spacers in sequence to form a strand. The strand can be seen in the channel with the unaided eye through a transparent window. Once the strand is arranged as desired, it is pushed into a sleeve that is held in a removable sleeve holder. If desired, the end portions of the filled sleeve may be cut off using a sleeve cutter to shorten the filled sleeve. The filled sleeve is implanted into patient using a needle.

20 Claims, 30 Drawing Sheets

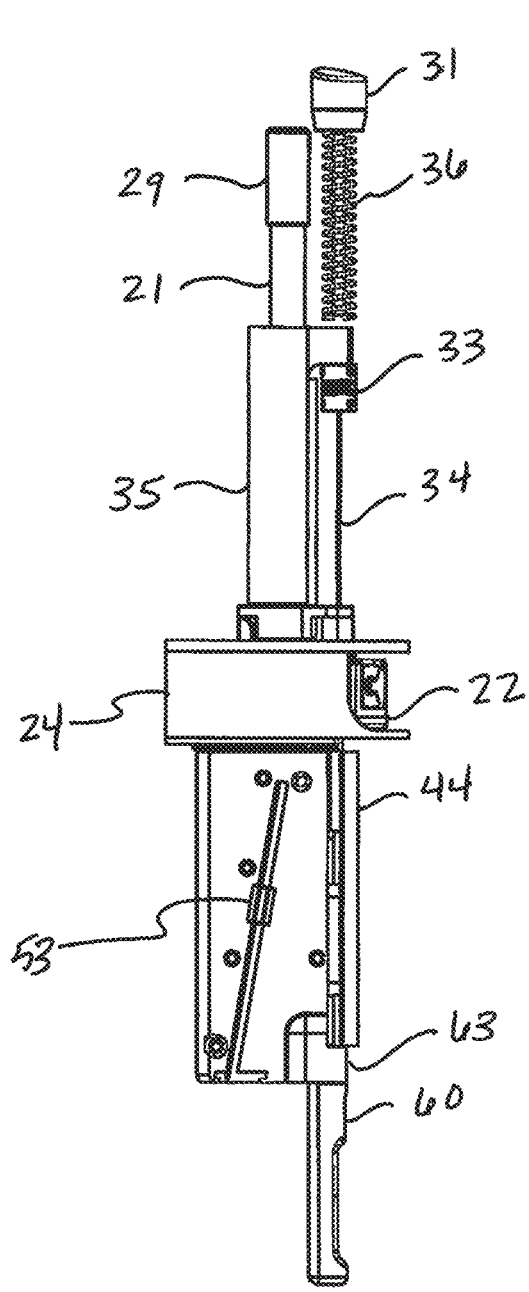
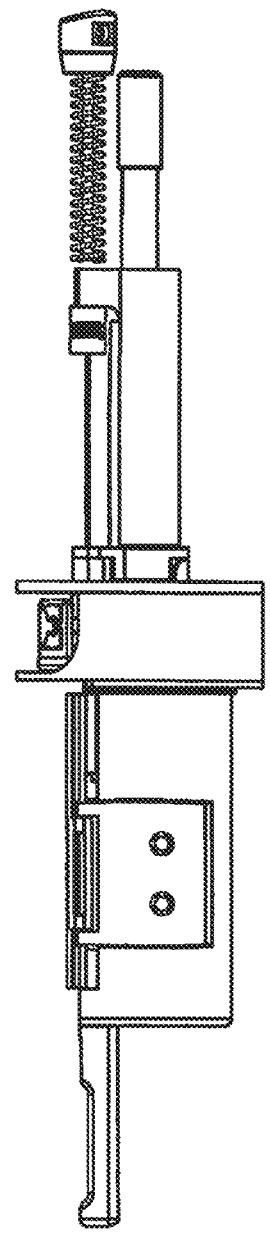
FIG. 3
FIG. 4

CUTTING DEVICE FOR BRACHYTHERAPY SEED IMPLANTATION SLEEVES

CROSS-REFERENCE TO RELATED APPLICATIONS

This application claims the benefit of co-pending U.S. patent application Ser. No. 16/165,178 filed Oct. 10, 2018, which claims priority to U.S. Provisional Application No. 62/580,837 filed Nov. 2, 2017.

FIELD OF INVENTION

This invention relates generally to a device for loading seeds and spacers into brachytherapy implantation sleeves. This invention relates particularly to a loader that easily switches from one pellet cartridge to another, and displays the sequence during loading.

BACKGROUND

Brachytherapy is the treatment of cancer by the insertion of radioactive implants directly into the tissue near the tumor. The implants are minute radioactive pellets known as seeds. The seeds and, optionally, non-radioactive pellets known as spacers, are lined up end-to-end in strands that are held together in a sleeve until implant. The pellets are held in the sleeve, which is placed in a needle and secured there by plugging the end with bone wax. The loaded sleeve is then inserted into the patient's tissue at the desired location.

Seeds of a given radioactive species and dosage are provided in a magazine, which in turn is held in a shielded case to protect humans from excess radiation exposure before and during the implant procedure. The seeds are extracted from the magazine and inserted into the sleeve. A variety of seed loaders exist for this purpose. The sleeve is inserted into a patient using a needle.

The amount of radiation to be delivered to the patient and placement pattern of the sleeves are determined in advance of the treatment. The sleeves are prepared accordingly, either pre-loaded per the irradiation plan before treatment or as the insertions are carried out during treatment. Once the treatment starts, the physician may determine that a different dosage or placement is needed, and the seeds and spacers need to be rearranged.

Loading a sleeve is a delicate process, and re-arranging the seeds and spacers as they go into a sleeve is very difficult. It would be desirable to have a loader that makes it easy to load seeds and spacers, and to easily rearrange them prior to inserting them into the sleeve.

SUMMARY OF THE INVENTION

This invention is a device for loading brachytherapy seeds and spacers into a sleeve. The device may hold two or more seed or spacer cartridges of different radioactive species and dosage. The user rotates a selector for selecting a desired cartridge and, with each depression of a spring-biased plunger, pushes a desired seed or spacer into a channel in an inspection area. The process is repeated for the desired number and order of seeds and spacers in sequence to form a strand. The seeds and spacers can be seen in the channel with the unaided eye through a transparent view window. The view window is part of a hinged door that can be opened and the sequence of the seeds and spacers rearranged with forceps, if necessary. Once the strand is arranged as desired, it is pushed into a sleeve that is held in a removable sleeve holder. Optionally the sleeve may be formed with pre-spaced compartments to hold each pellet in a spaced relationship with the other seeds as they are pushed into place. If desired, the end portion of the filled sleeve may be cut off using a sleeve cutter in order to shorten the filled sleeve. The filled sleeve is implanted into patient using a needle.

BRIEF DESCRIPTION OF THE DRAWINGS

FIG. 3 is a left side view of the device in FIG. 1.

FIG. 4 is a right side view of the device in FIG. 1.

DETAILED DESCRIPTION OF THE INVENTION

Figure 1:
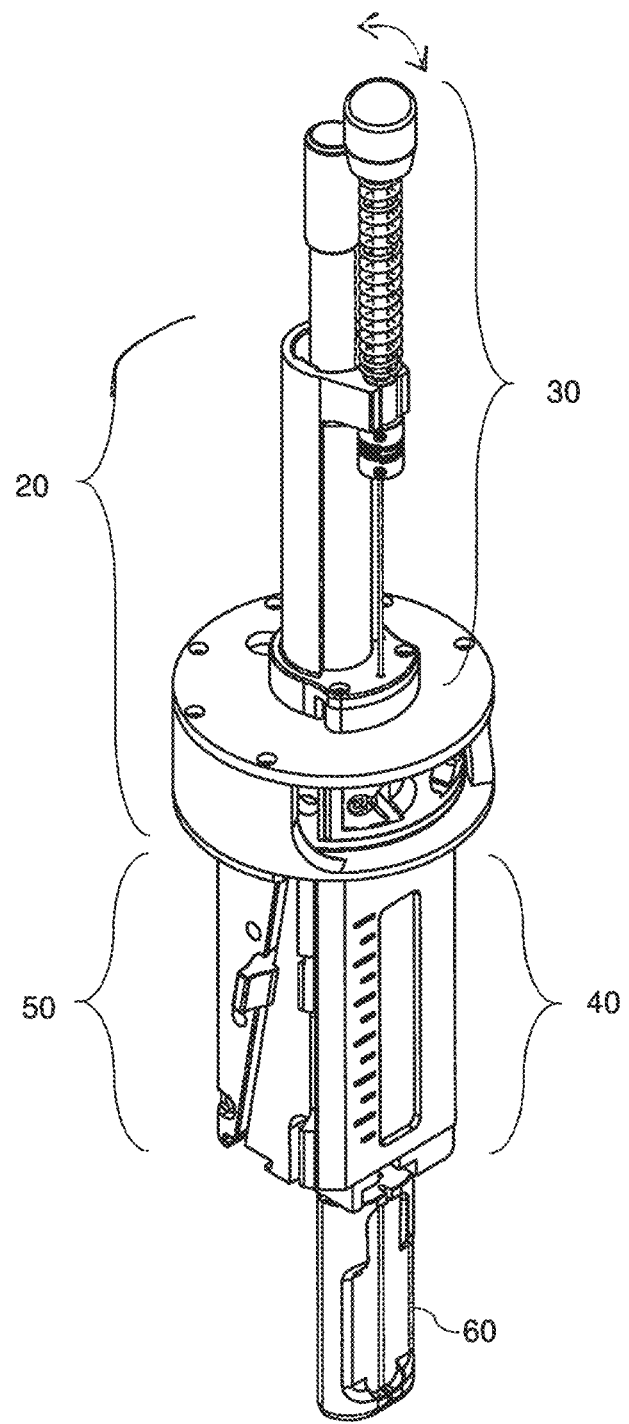
FIG. 1 is a top perspective view of a first embodiment of the present invention.
Figure 2:
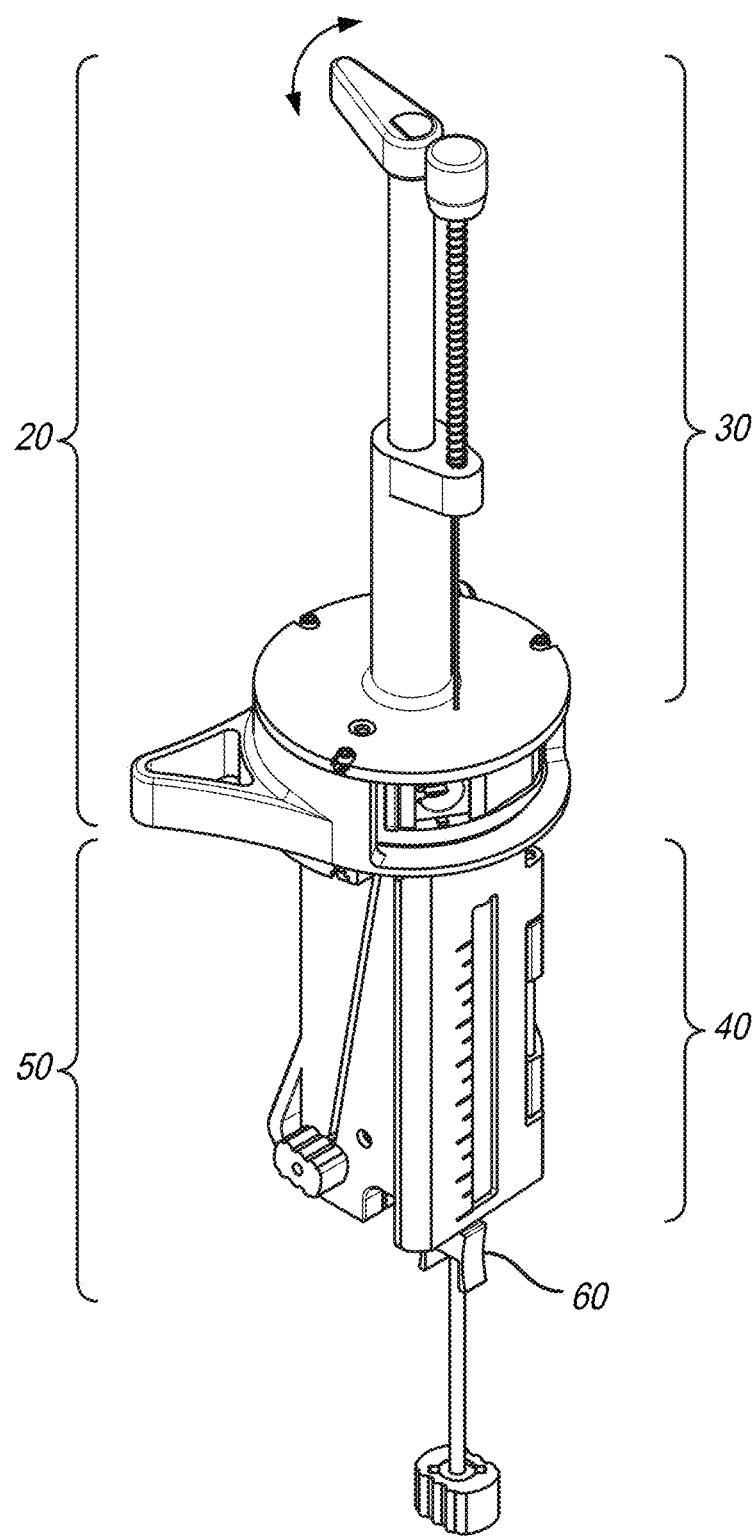
FIG. 2 is a top perspective view of a second embodiment of the present invention.
Figure 5:
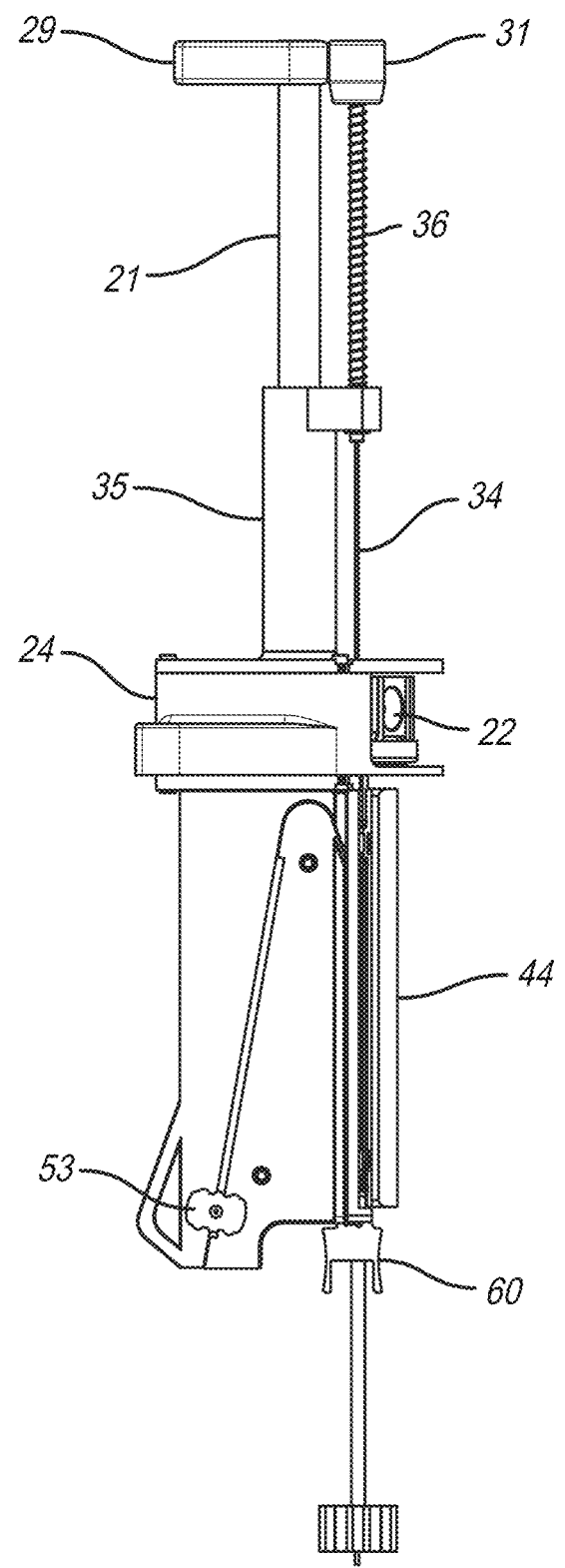
FIG. 5 is a left side view of the device in FIG. 1.
Figure 6:
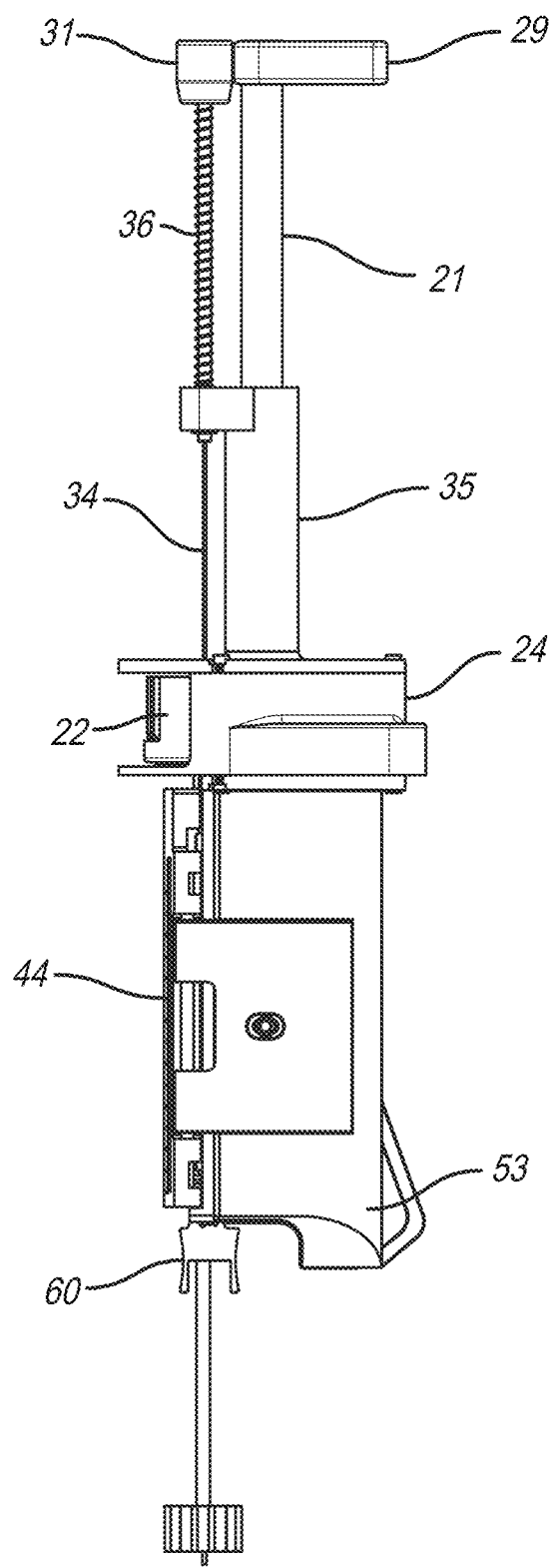
FIG. 6 is a right side view of the device in FIG. 1.
Figure 7:
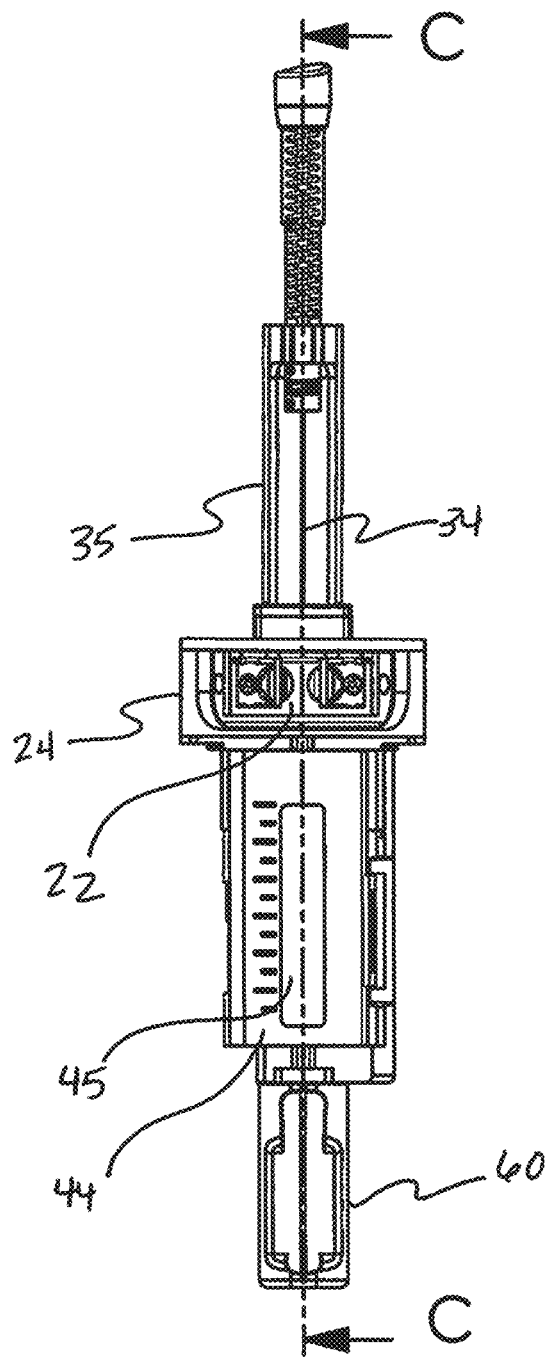
FIG. 7 is a front view of the device in FIG. 1.
Figure 8:
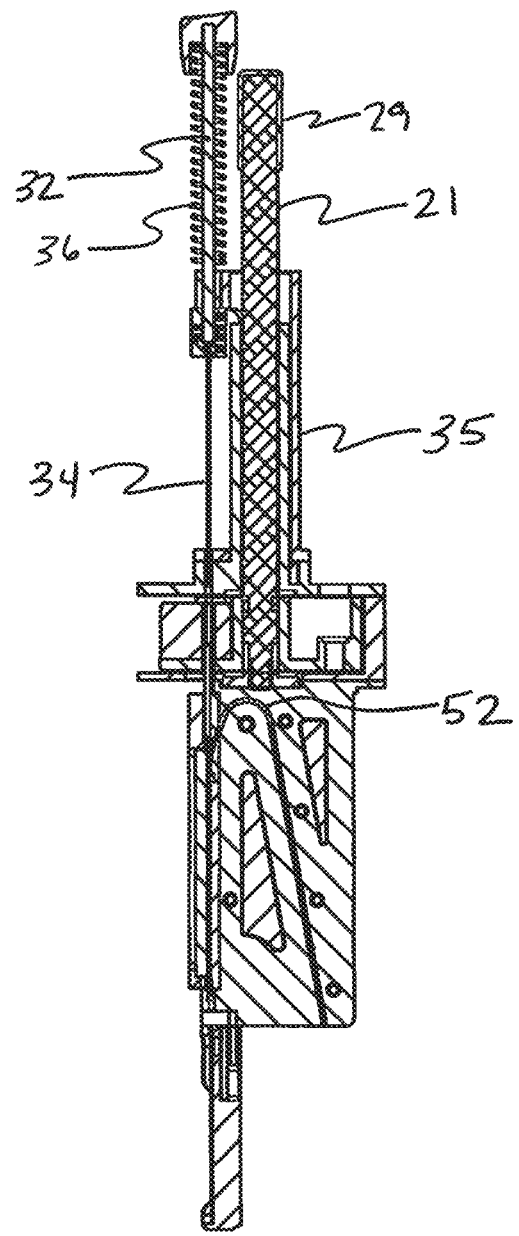
FIG. 8 is a cross-section view along line C-C of FIG. 7.
Figure 9:
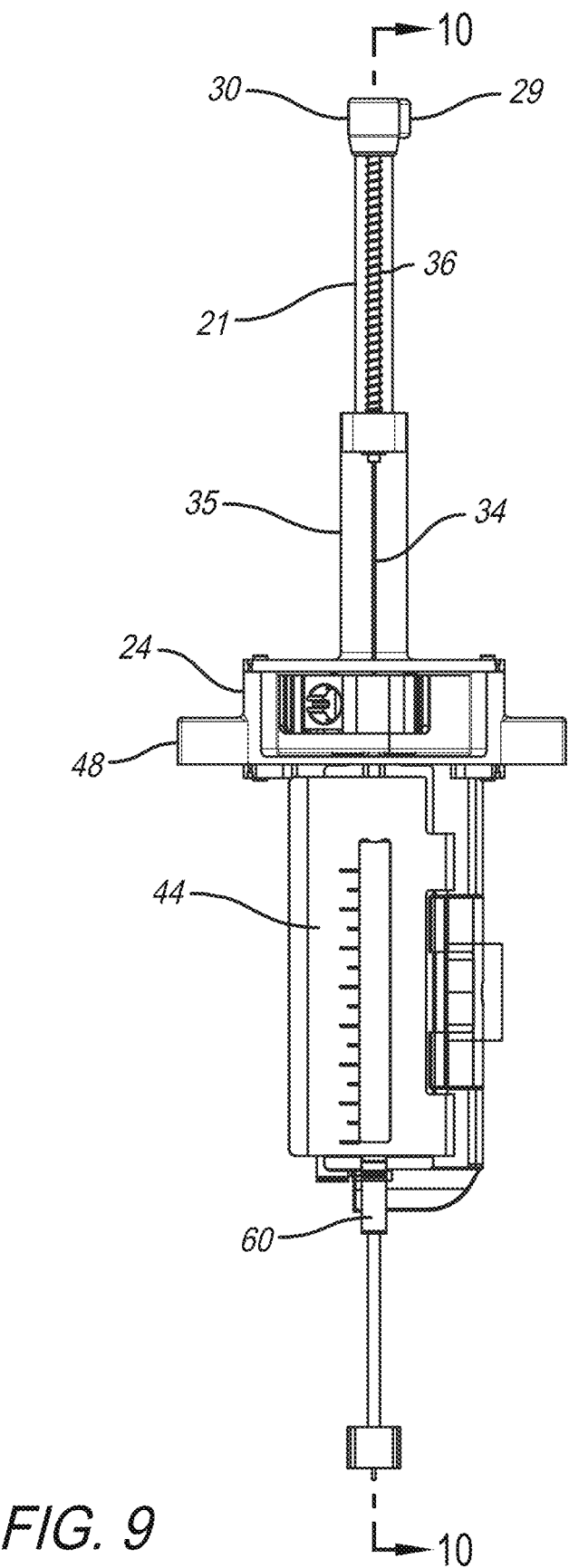
FIG. 9 is a front view of the device in FIG. 2.
Figure 10:
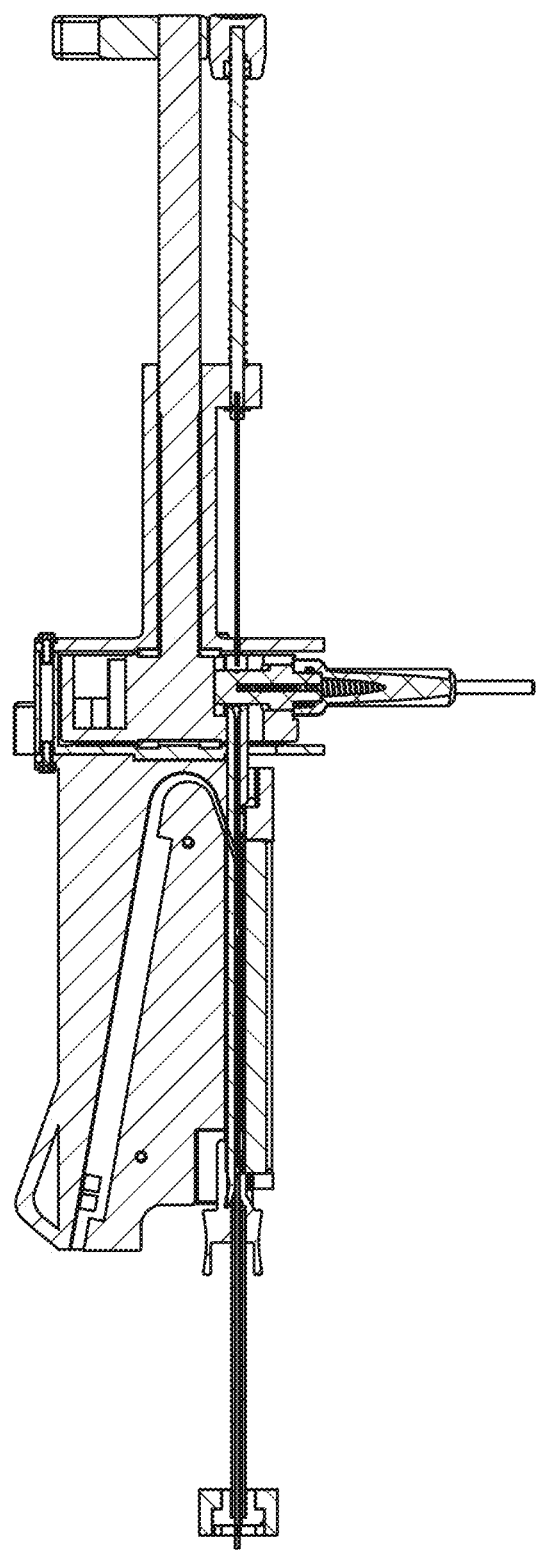
FIG. 10 is a cross-section view along line D-D of FIG. 9.
Figures 11, 12:
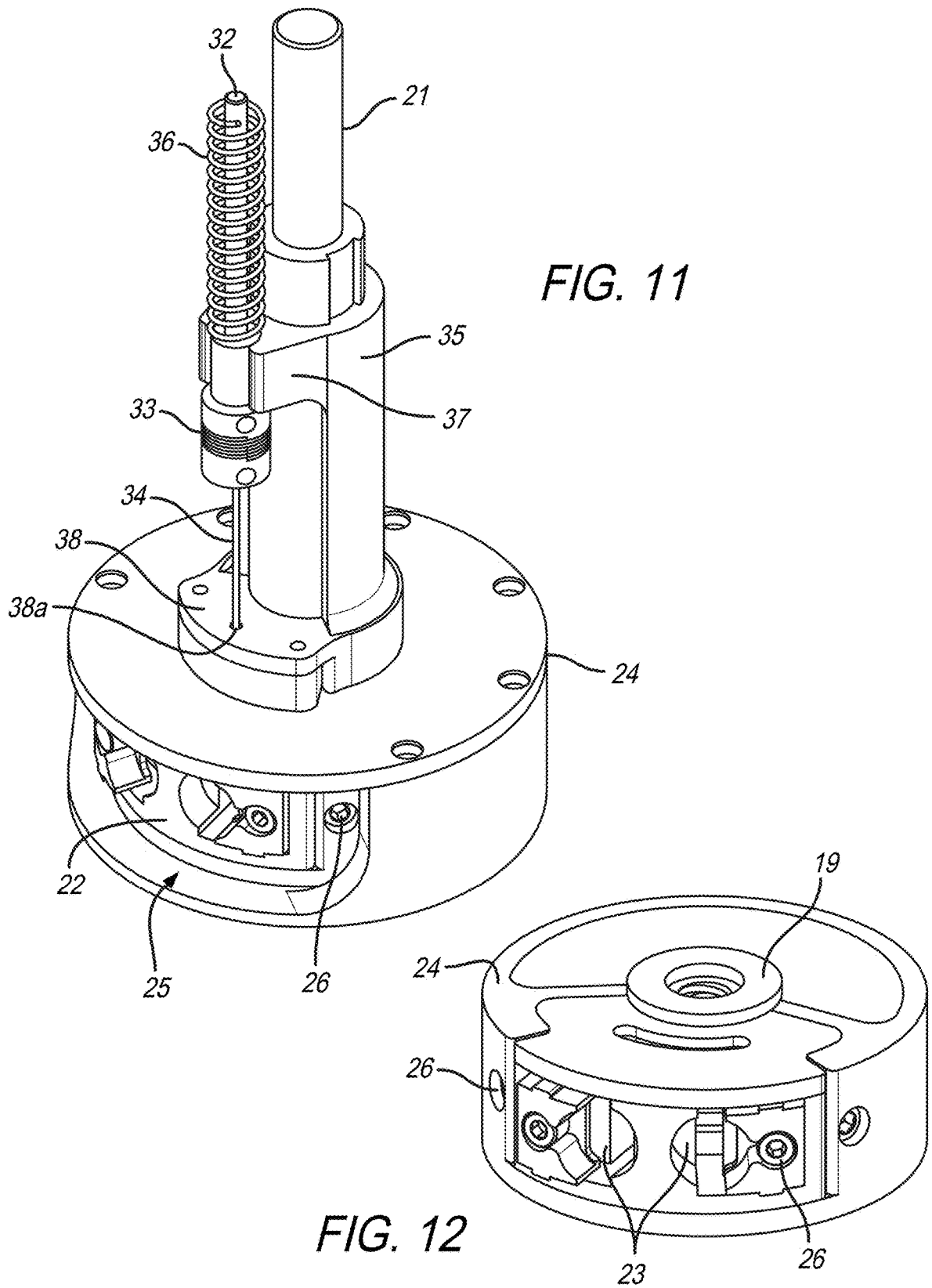
FIG. 11 is a top perspective view of the turret assembly of the first embodiment of the present invention.
FIG. 12 is a top perspective view of the turret of the first embodiment of the present invention.

The invention is for loading brachytherapy seeds and spacers from one or more cartridges 9 into an implantable insertion sleeve 62 and cutting the sleeve to a desired length. The loading device and cutter are configured to be hand-held or removably affixed to a table or countertop. One embodiment of the loader has stand legs 48 to support the device on a table or countertop. Alternatively the loader and cutter can be supported on a table or countertop with a jig (not shown).

The loading device has four assemblies that cooperate to arrange and load the seeds and spacers, which are alternatively and collectively referred to herein as pellets 7. A turret assembly 20 enables a user to select a desired cartridge 9. A plunger assembly 30 pushes a pellet 7 from the cartridge 9 into a channel 41 in an inspection assembly 40. The inspection assembly 40 receives the pellets end-to-end and permits the user to view the strand 61 as it is being built. A strand pusher assembly 50 pushes the strand 61 into the sleeve 62 which is held in a removable sleeve holder 60. The sleeve 62 is a hollow tube, also known the art as a straw. The filled sleeve 62 is removed from the sleeve holder 60 and implanted into patient using a needle (not shown) at the time of radiation treatment. The passageway for the pellets' travel is in fluid communication between a first open end in the turret assembly through the inspection assembly and into the sleeve. Preferably the passageway is straight, but may have bends or curves. FIGS. 1-10 show two embodiments of the loading device with the assemblies connected to each other, along with the attached sleeve holder.

The loading device is modular so that several of the assemblies and subassemblies can be easily removed and replaced with parts having similar functions but different shapes and sizes, which permits the device to accommodate a wide variety of cartridges, pellets, and sleeves. For example, the pellets may be of different radioactive materials or of non-radioactive materials, the pellets may have different lengths and diameters, the sequence length may be longer or shorter, and the sleeves may be made of a variety of sleeve materials. The modularity in turn permits different types of treatment designs for pellet placement in different areas of the body.

The turret assembly 20 comprises a selector rod 21 fixed to the turret head 22, which is disposed in a rotatable relationship within a turret housing 24. See FIGS. 11, 12, 14, and 15. As used herein, a fixed relationship means that the parts are static relative to one another when connected, although fixed parts may be separable to permit easy replacement with similar parts. As used herein, a rotatable relationship means that the parts are rotatable relative to one another when connected. The rotatable parts may also be separable to permit easy replacement with similar parts.

The turret head 22 has two or more head apertures 23 along its perimeter to receive two or more cartridges 9. The turret housing 24 has at least one housing aperture 25 along its perimeter to permit the cartridges 9 to be inserted through the turret housing 24 into the turret head 22. The turret head 22 and turret housing 24 each have a top thru-slot 27 and a bottom thru-slot 28, respectively, that permit a plunger pin 34 to travel through the turret housing and turret head 24 into a cartridge 9 to eject a pellet into the inspection assembly, as described in more detail below. Optionally, adjustment screws 26 allow for individual depth adjustment of each cartridge 9.

Figure 34:
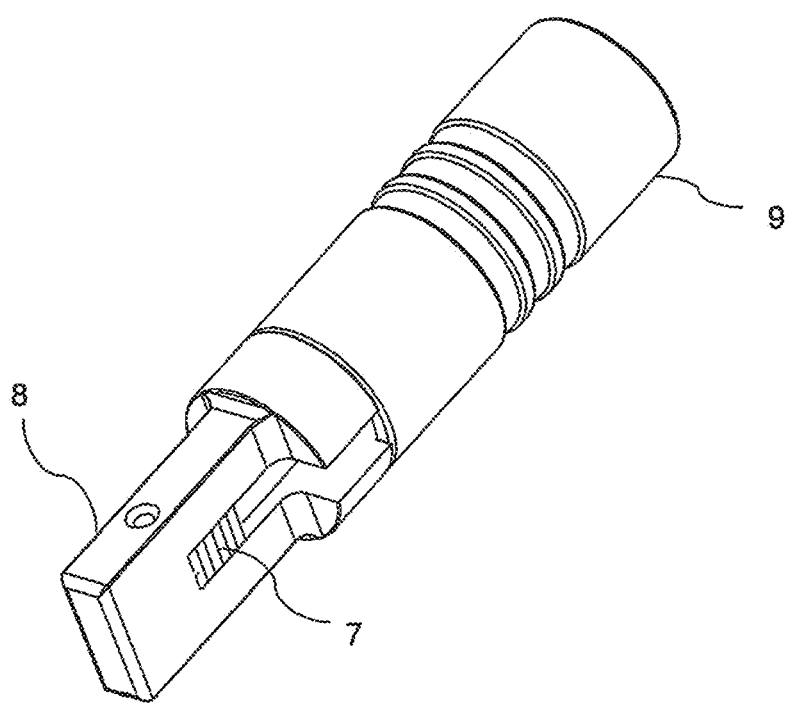
FIG. 34 is a perspective view of a Mick® cartridge of the prior art.

The head apertures 23 are shaped to mate with the desired cartridge 9. Mick® cartridges, shown in FIG. 34, are cylindrical and commercially available. The magazine 8 holding the pellets 7 inside the Mick® cartridge has a rectangular cross section. In the preferred embodiment the cartridges are cylindrical and are mated to circular head apertures 23 in the turret head 22, as shown in FIGS. 11, 12, 14, and 15. In other embodiments the head apertures 23 have a rectangular or square shape to mate with cartridges having rectangular or square cross-section, respectively. Turret heads 22 are interchangeable with in the turret housing 24, making the loading device easily compatible with multiple shapes and types of cartridges.

The turret assembly 20 and plunger assembly 30 cooperate to enable the plunger assembly 30 to be rotated relative to the turret head 22. A low friction bushing 19 may be employed at the interface of the turret head 22 and the turret housing 24 to enable quick rotation without causing wear to the surfaces. Visual indicators such as hash marks may be employed to show when the plunger pin 34 is properly aligned over the cartridge 9. A detent mechanism may be employed at the interface of the turret head 22 and the turret housing 24 to assure that the plunger pin 34 is properly aligned over the cartridge 9 and to give a tactile indication to the user that alignment is proper.

The plunger assembly 30 comprises a hollow plunger tower 35 that is fixed to or integral with the turret housing 24. In one embodiment shown in FIG. 11, the plunger tower 35 is attached to the turret housing at a base 38. In a second embodiment shown in FIG. 14, the plunger tower 35 is attached to the turret housing without a base 38. The turret housing 24 has a thru-hole 38a to receive the plunger pin 34, which in turn will eject a pellet from the selected cartridge. In the embodiment with the base, the base has a thru-hole co-axial with the thru-hole in the turret housing to receive the plunger pin 34. In the preferred embodiment the plunger tower 35 is co-axially aligned with the turret head 24, but in other embodiments it may be off-center. See FIG. 6. The plunger assembly 30 further comprises a guide collar 37 to hold a plunger subassembly 39 along an axis that is offset from, but parallel to, the axis of the plunger tower, and that is aligned with the channel 41 in the inspection assembly 40. See FIG. 8.

Figure 17:
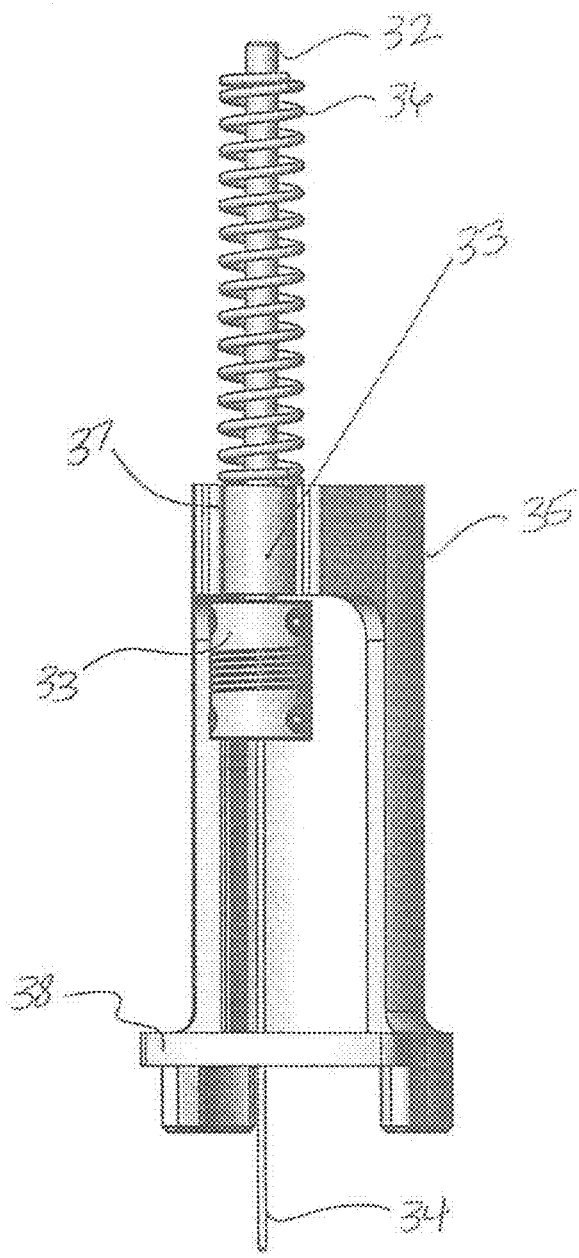
FIG. 17 is a front view of the plunger assembly of the first embodiment of the present invention.
Figure 18:
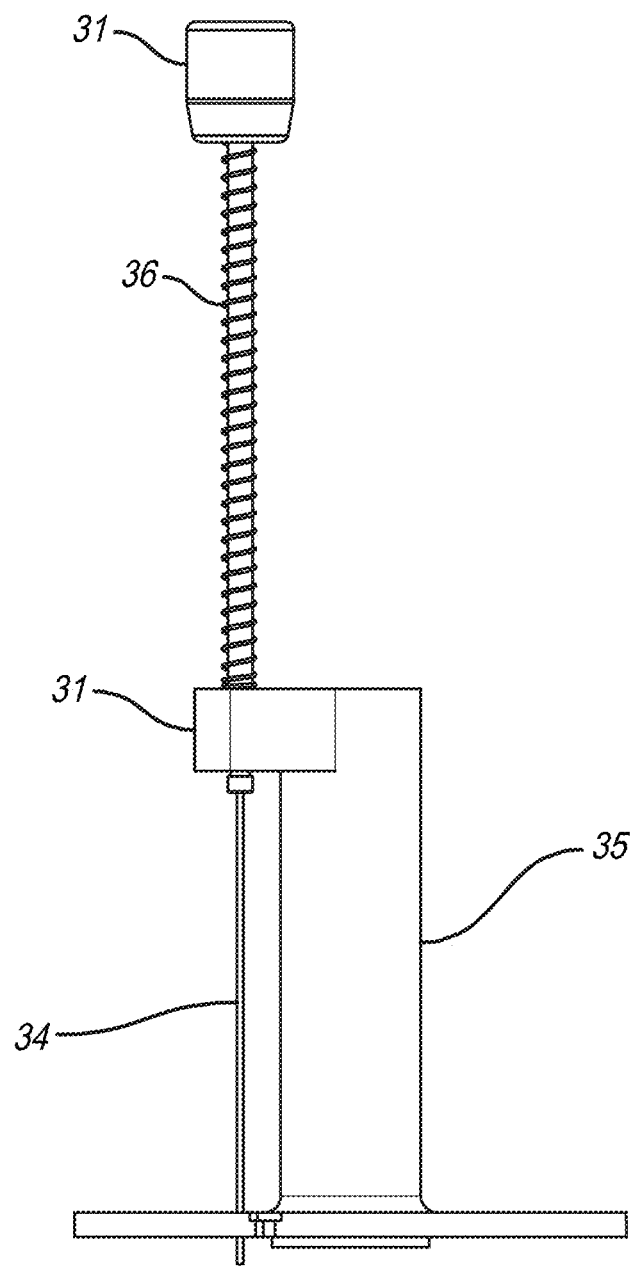
FIG. 18 is a front view of the plunger assembly of the second embodiment of the present invention.
Figure 20:
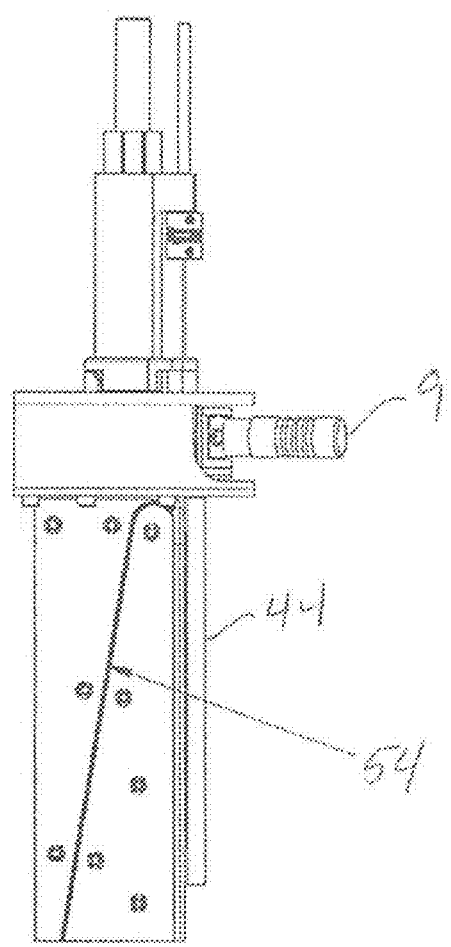
FIG. 20 is partial side view of the first embodiment of the present invention.
Figure 21:
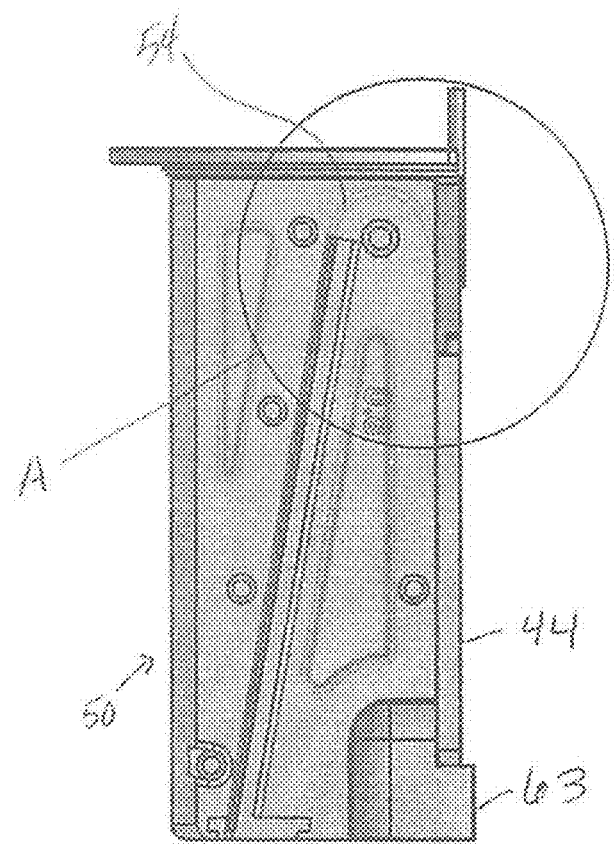
FIG. 21 is a close-up side view of the strand pusher assembly.

The plunger subassembly 30 comprises a plunger 32, a coupler 33, a plunger pin 34, and a spring 36, all co-axially aligned and held in fixed relationship to the plunger tower 35 by the guide collar 37. See FIGS. 17 and 18. The plunger 32 is spring biased in an "up" position, with the plunger pin 34 retracted from the cartridge. The plunger subassembly optionally and preferably also comprises a plunger cap 31 that provides a surface for a user's finger to have certain purchase on the plunger. The coupler 33 may hold the plunger at a set resting depth, or may enable the resting depth to be adjusted by about 1-4 mm. A coupler 33 also allows easy replacement of the plunger pin 34.

Figure 13:
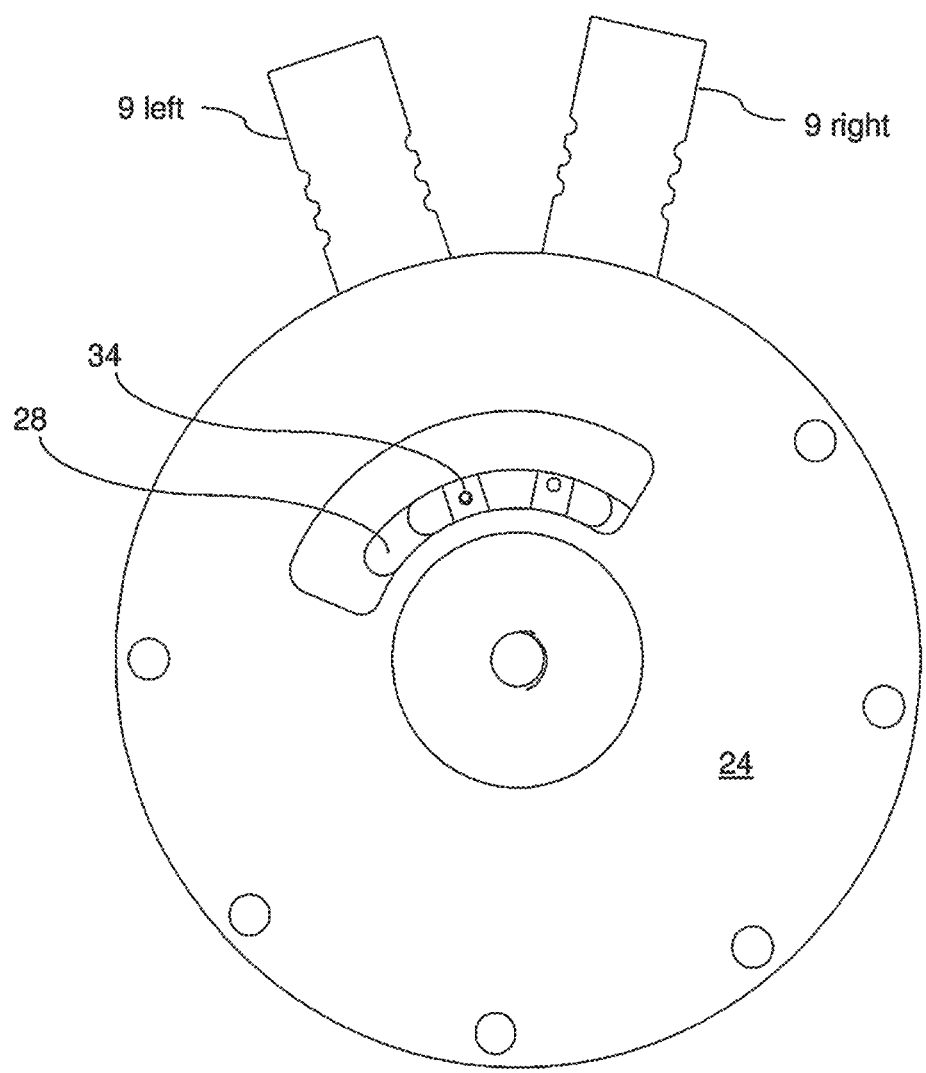
FIG. 13 is a bottom perspective view of the turret of the second embodiment of the present invention.
Figure 14:
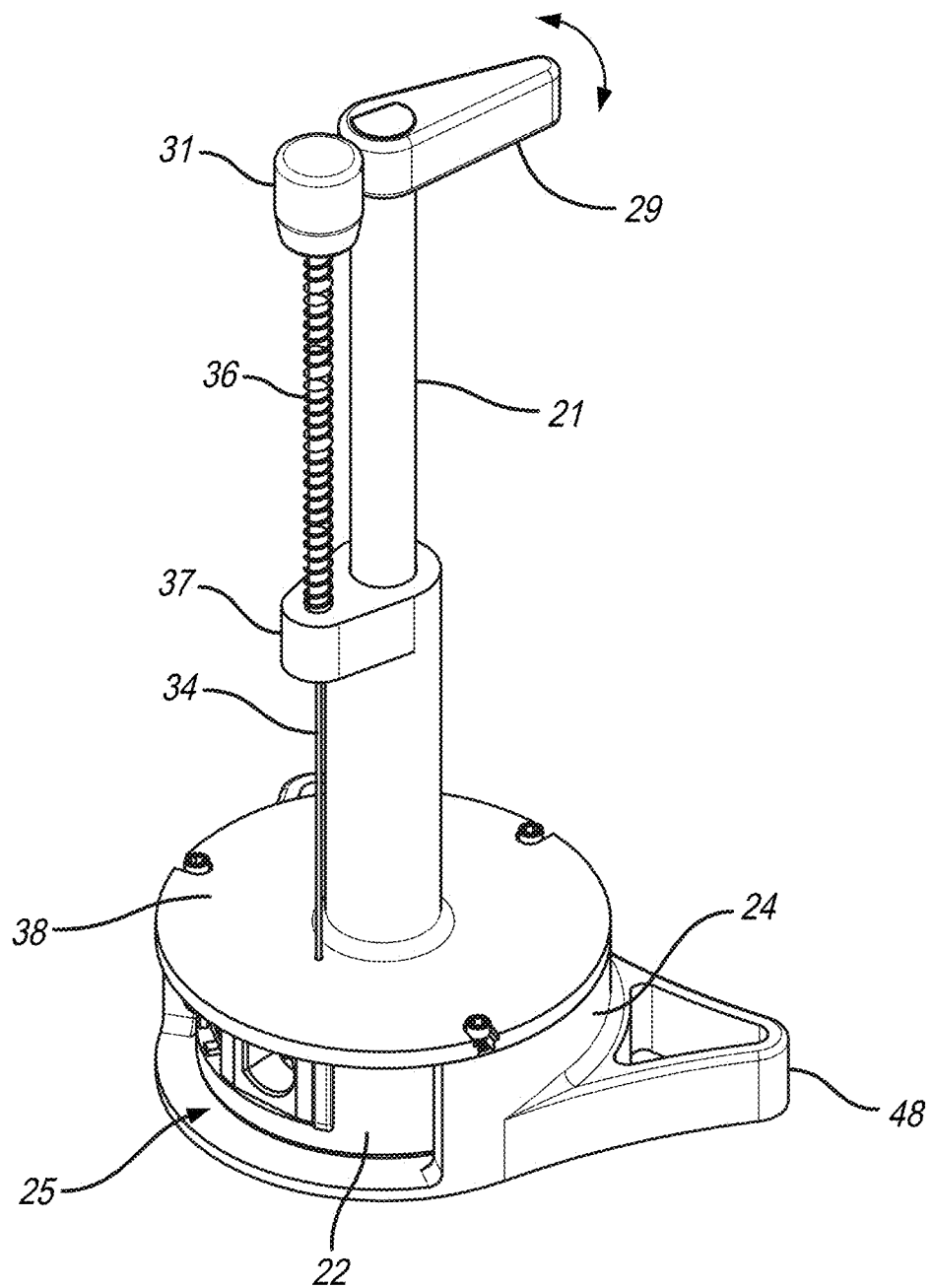
FIG. 14 is a top perspective view of the turret assembly of the second embodiment of the present invention.
Figure 15:
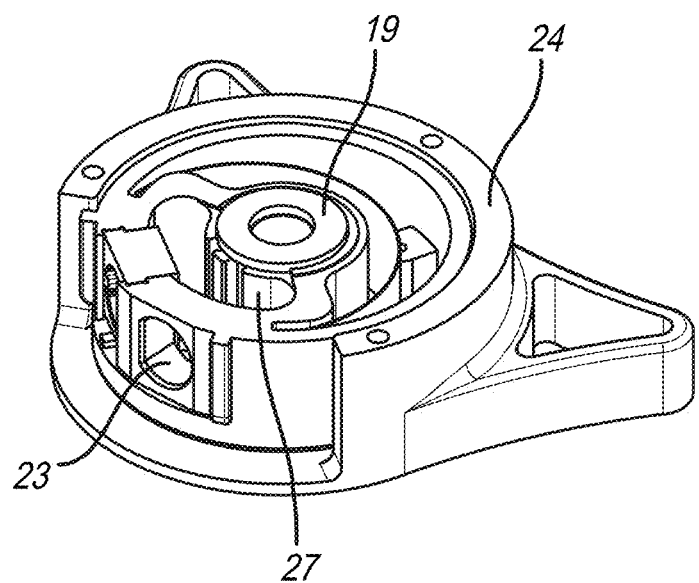
FIG. 15 is a top perspective view of the turret of the second embodiment of the present invention.
Figure 16:
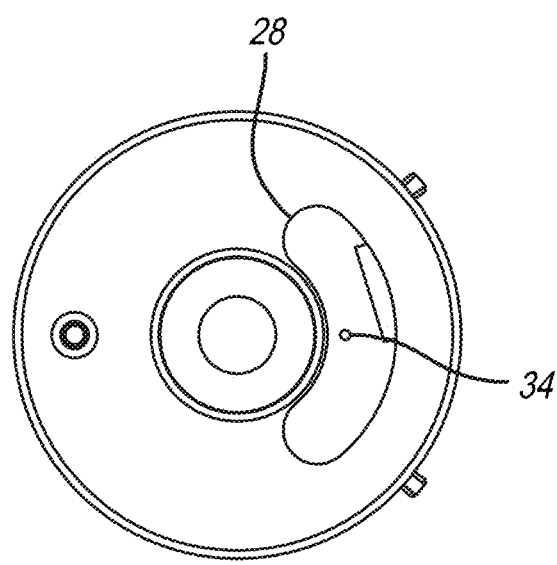
FIG. 16 is a bottom perspective view of the turret of the second embodiment of the present invention.
Figure 30:
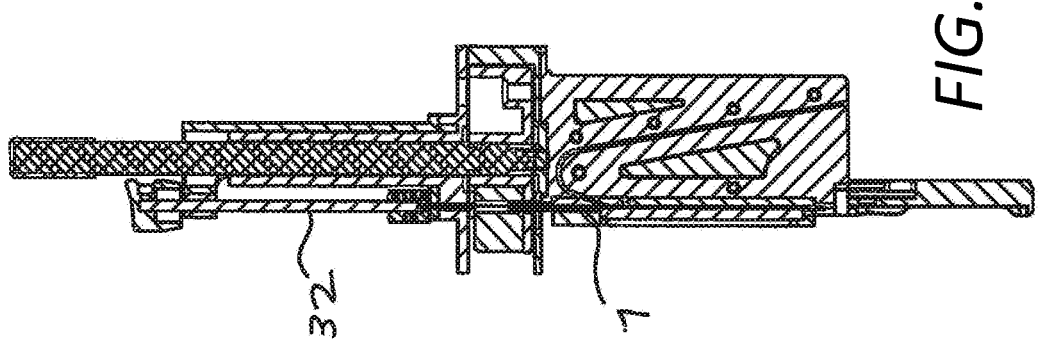
FIG. 30 is a front cross-section of the device with Mick® cartridges inserted and the plunger in the up position.
Figure 29:
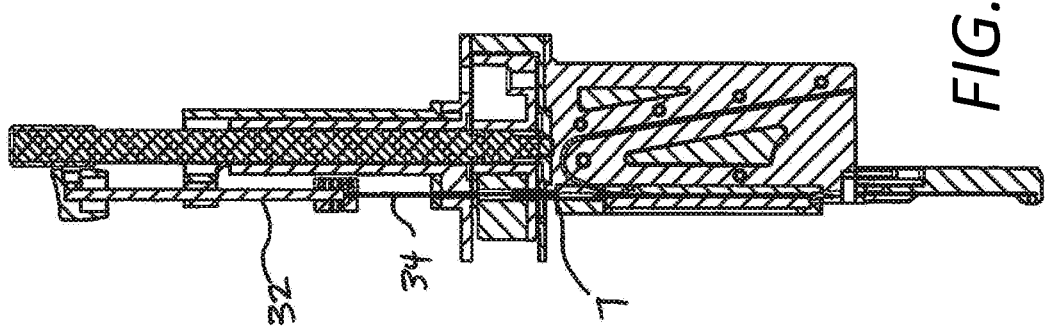
FIG. 29 is a front cross-section of the device with Mick® cartridges inserted and the plunger in the up position.
Figure 28:
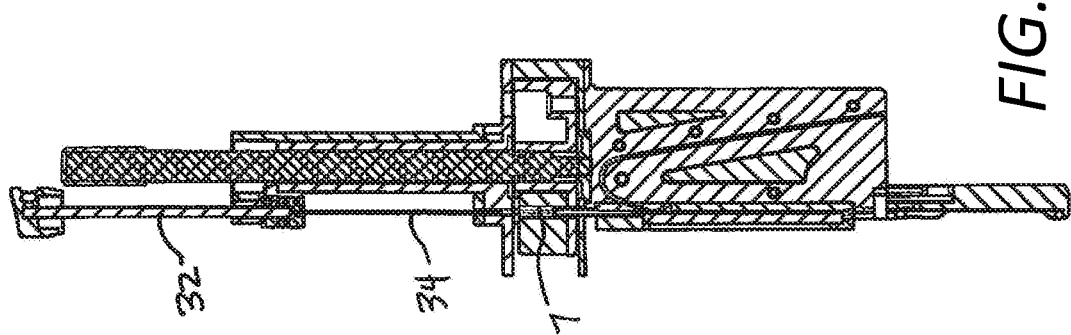
FIG. 28 is a front cross-section of the device with Mick® cartridges inserted and the plunger in the up position.

The selector rod 21 is co-axially aligned in the plunger tower 35 and rotates within the plunger tower to turn the turret head 22 to align the desired cartridge over the channel 41 in the inspection assembly 40. FIG. 13 shows the bottom view of the turret head 22 rotated to select the cartridge 9a on the right in a first embodiment of the loading device. FIG. 16 shows the bottom view of the turret head 22 rotated to select the cartridge 9a on the right in a second embodiment of the loading device. The selector rod 21 optionally and preferably also comprises a selector rod cap 29 that provides a lever or knurled surface for a user's fingers to more easily grip the selector rod. The user rotates the selector rod 21 for selecting a desired cartridge, as shown by the arrow in FIGS. 1 and 2. With each depression of a spring-biased plunger 32, the user pushes a desired seed or spacer into a channel 41 in an inspection area. FIGS. 28-30 show cross-sectional views of the loading device as the plunger is pressed down, moving the plunger pin 34 from the turret housing 24 through the turret head 22, the cartridge, and finally into the channel 41 of the inspection assembly 40. The full stroke of the plunger places the pellet at a distance from the selected cartridge sufficiently far from the cartridge body that moving the turret will not contact or damage the pellet or selection mechanism. The spring forces the plunger subassembly 39 back to its resting position and the process of rotation and pellet ejection is repeated for the desired number and order of seeds and spacers in sequence to form a strand. Alternatively, the plunger may be moved and retracted by means other than a spring, such as manually using a detent system.

Figure 19:
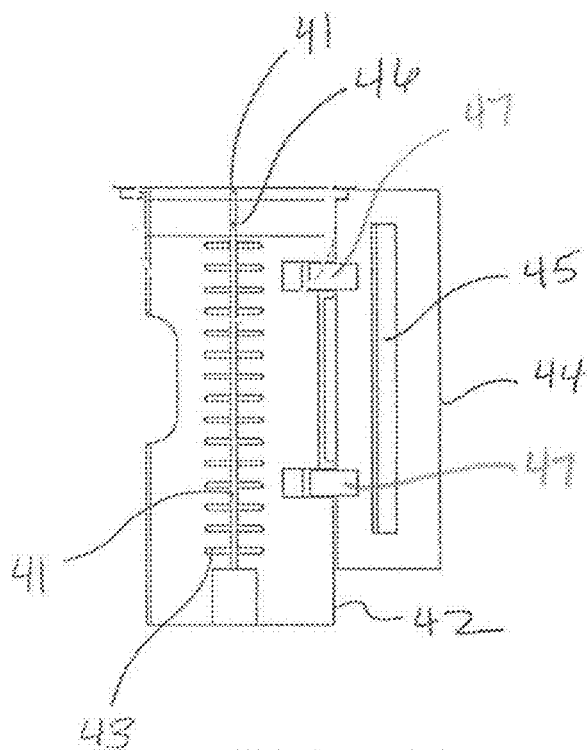
FIG. 19 is a front view of the inspection assembly of the first embodiment of the present invention with the door open.
Figure 27:
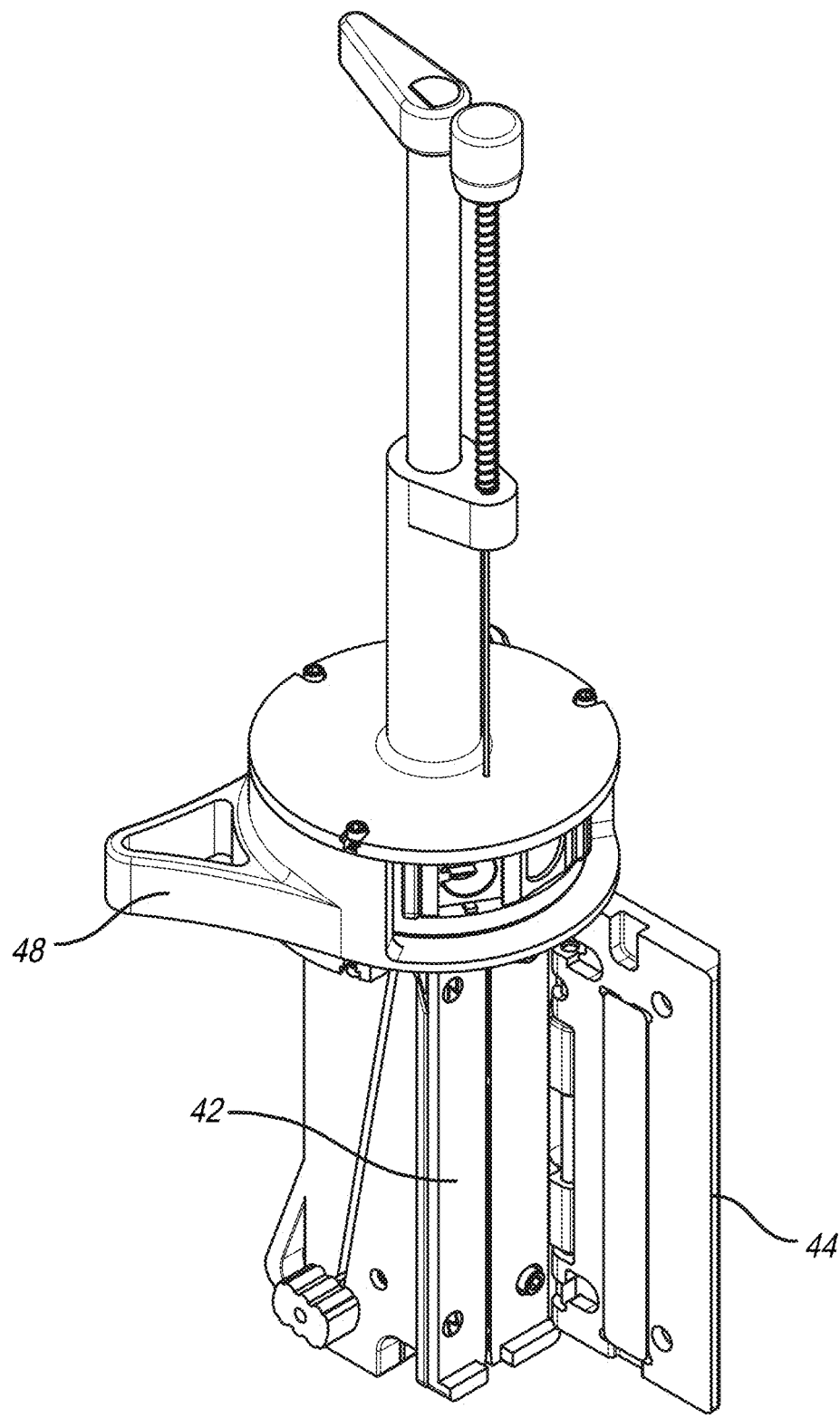
FIG. 27 is a top perspective view of a portion of the second embodiment of the device with Mick® cartridges inserted and the door open.

The inspection assembly 40 is fixed to the turret housing 24. It comprises a flat plate 42 into which a channel 41 is indented to receive the pellets. See FIGS. 19 and 27. Optionally, the plate has forceps slots 43, which are grooves that are sized and oriented to facilitate forceps picking up an individual pellet from the channel 41. As used herein, forceps refers to any type of device that can move a single seed, including for example forceps, tweezers, pincers, or a pick. The slots 42 enable the tips of the forceps to fit into the slot below the surface of the plate 42, which helps secure the aim and grip on the tiny pellet while it is in the channel 42. The forceps slots 43 may be indentations in the plate that do not go all the way through the thickness of the plate 42, or they may be through-holes. The flat plate 42 also comprises a thru-hole 46 that is in communication with the strand-pusher assembly 50, as described in more detail below.

Figure 24:
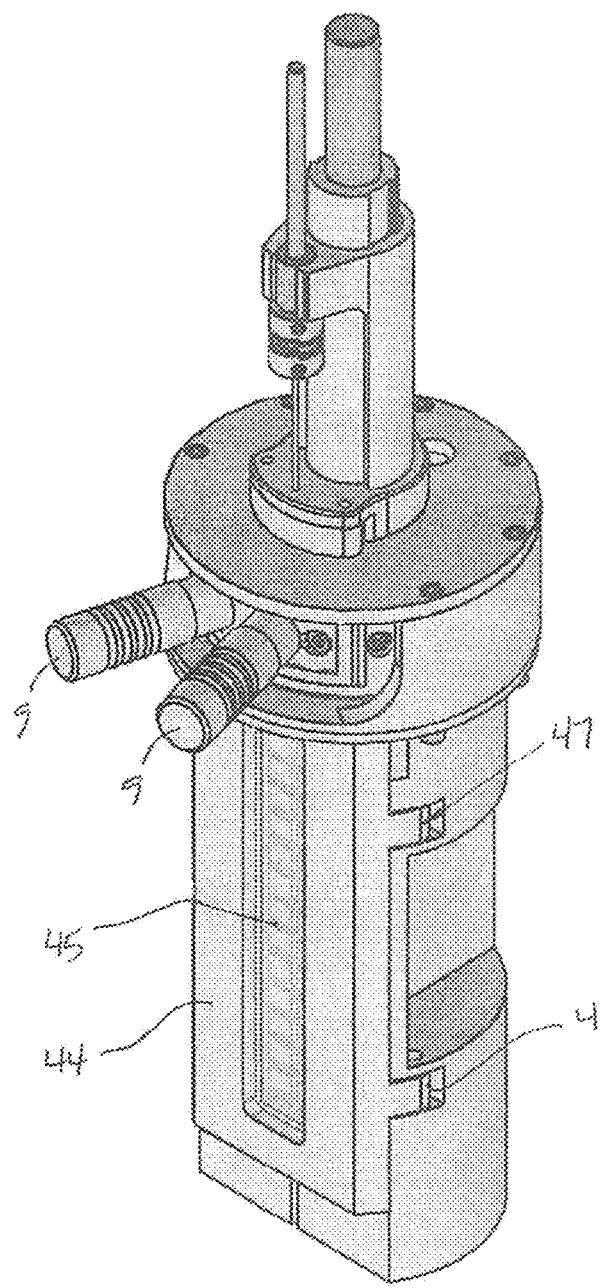
FIG. 24 is a top perspective view of a portion of the first embodiment of the device with Mick® cartridges inserted and the door closed.
Figure 25:
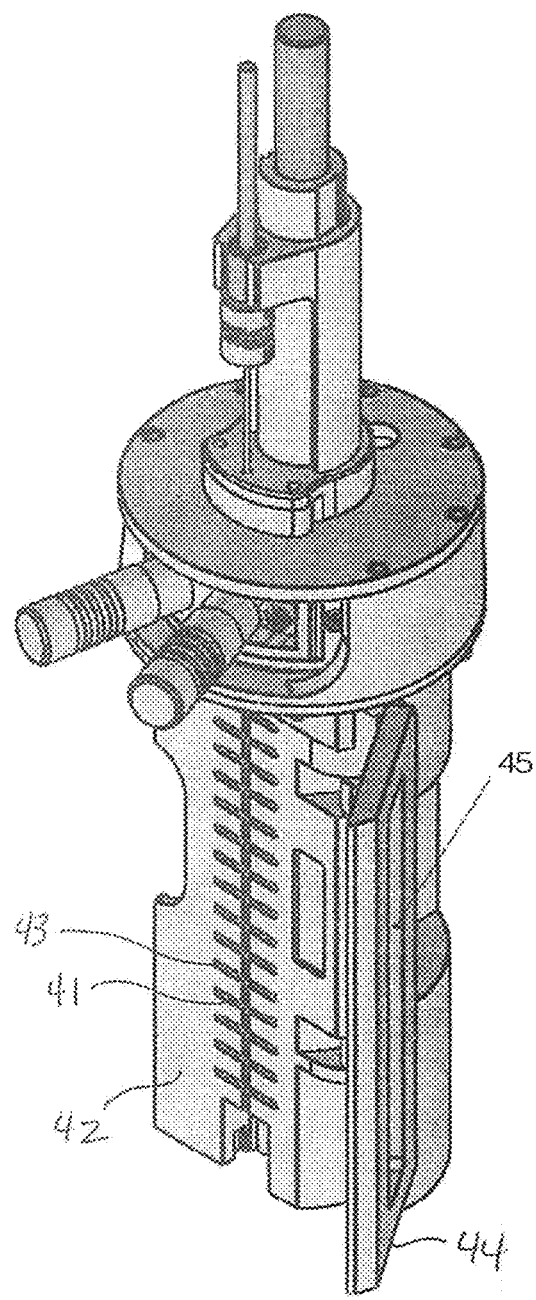
FIG. 25 is a top perspective view of a portion of the first embodiment of the device with Mick® cartridges inserted and the door open.
Figure 26:
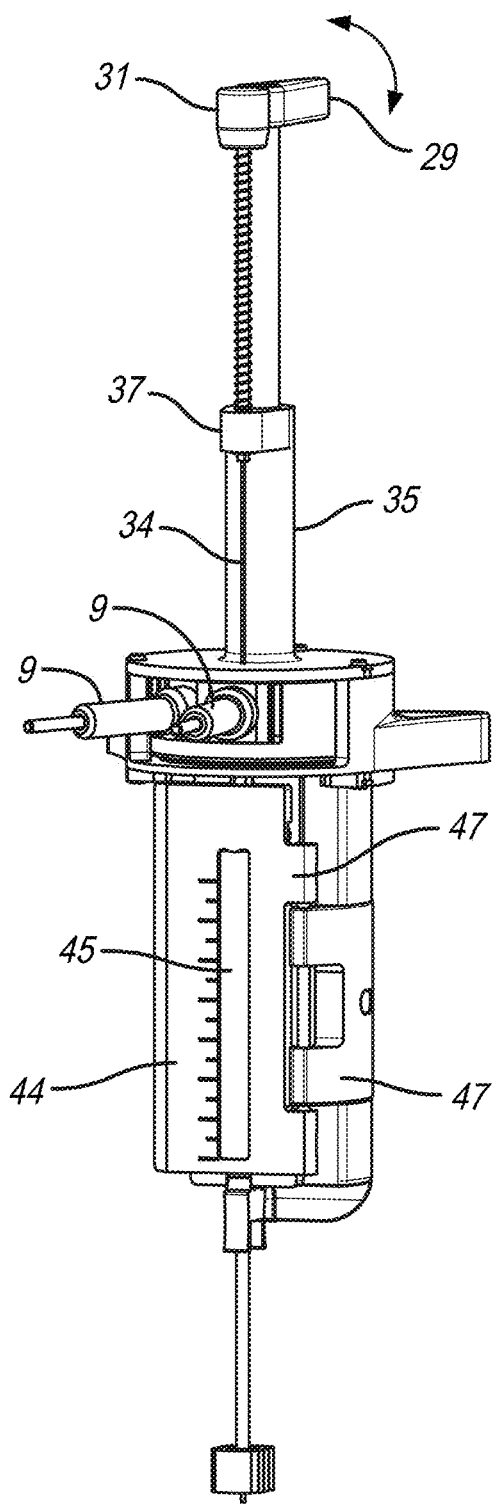
FIG. 26 is a top perspective view of a portion of the second embodiment of the device with Mick® cartridges inserted and the door closed.

The inspection assembly 40 further comprises a hinged door 44 which encloses the channel and the sequence when it is closed so that the pellets cannot fall out of the channel 41. The door 44 may have a transparent portion 45 that permits the user to see the seeds and spacers with the unaided eye while the door 44 is closed, as the strand is being built. The transparent portion is preferably a slot window, as shown in FIGS. 24-26, or the transparent portion may as large as the entire door 44. The door may have markings 49 for calibrations.

The door 44 is attached to the plate 42 at hinges 47. When the door is closed the channel is enclosed and any pellets therein are held securely. The user can open the door 44 to access the pellets in the channel 41, and use forceps (not shown) to remove a seed or spacer or rearrange the sequence before the strand is pushed into the sleeve 62. This enables the user to adjust the radiation treatment plan intraoperatively, with real-time creation of each strand. The user then closes the door and continues building the sequence of seeds and spacers.

Figure 22:
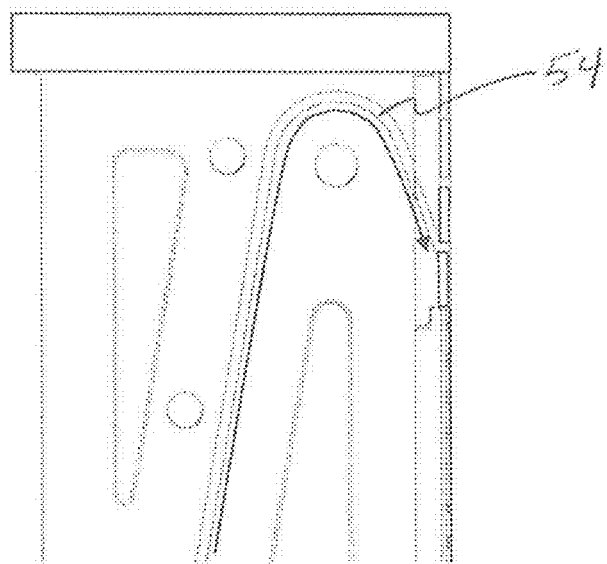
FIG. 22 is a close-up view of area A indicated in FIG. 21.
Figure 23:
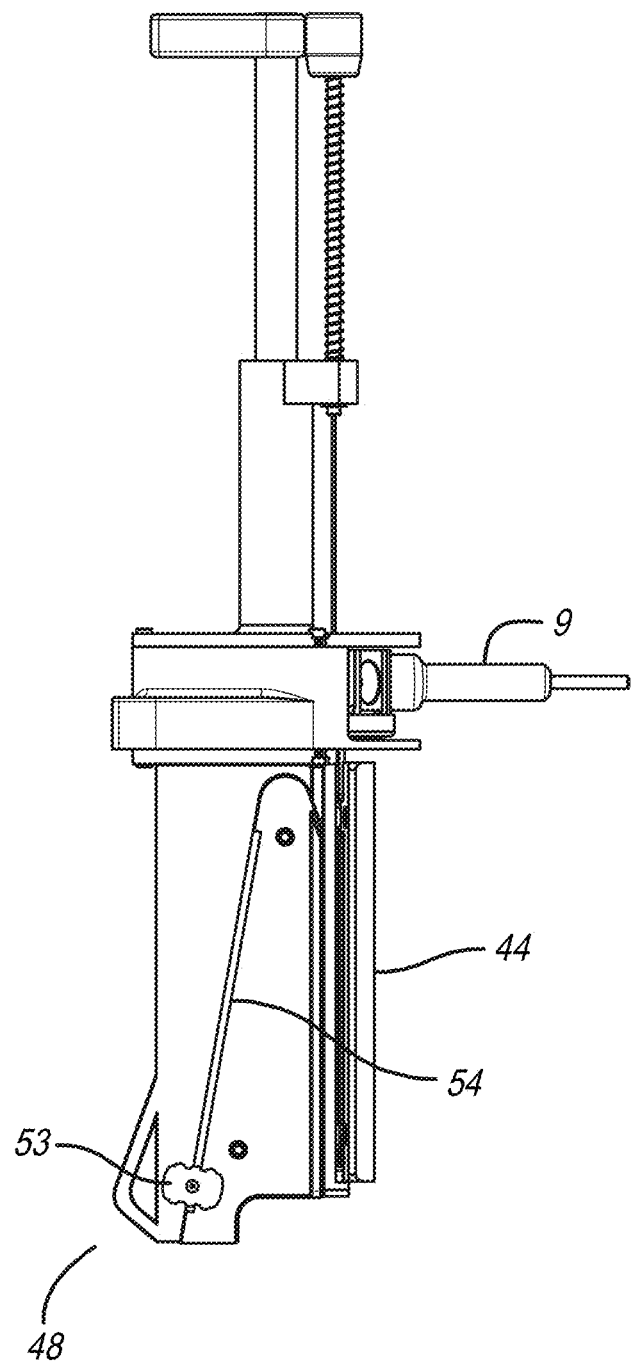
FIG. 23 is partial side view of the second embodiment of the present invention.

A strand-pusher assembly 50 is fixed to the inspection assembly 40. See FIGS. 1 and 2. The strand-pusher assembly 50 uses a mechanism to physically push the sequence into the awaiting sleeve 62 in the sleeve holder 60. In a preferred embodiment, the strand-pusher assembly 50 comprises a dispensing wire 51 seated in an arcuate channel 52. See FIGS. 20-23. The path of the wire is indicated by the arrow in FIG. 22. The dispensing wire 51 is deformable, resilient and flexible, and is preferably nitinol. A tab 53 is fixed to the wire 51 through a tab slot 54 and is used to push the wire 51 along the channel 52 and through the thru-hole 46 of the inspection plate 42. By moving the tab 53, the wire 51 bends in the arcuate channel and contacts the proximate end of the sequence that is in the inspection channel 41. Pushing the tab 53 further forces the wire 51 to ease the sequence into the awaiting sleeve 62 in the sleeve holder 60. The dispensing wire 51 is returned to its original position before the next sequence of seeds is created. In another embodiment, in lieu of the arcuate channel and separate nitinol wire, a dispensing wire slidably mated to the door is used to plunge the sequence into the sleeve 62.

Figure 31:
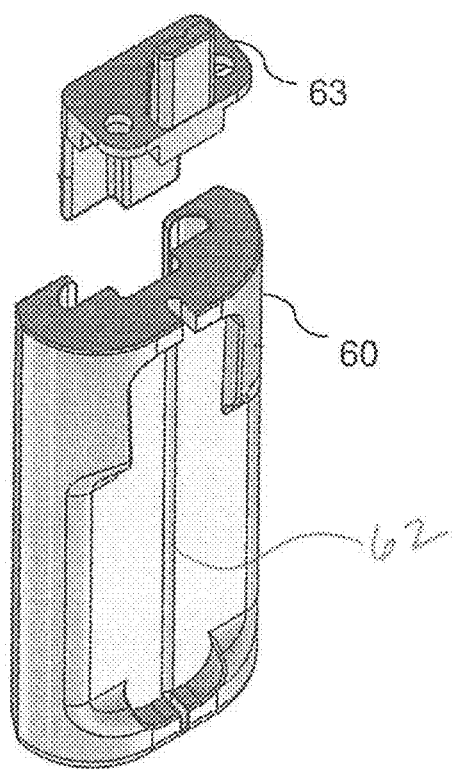
FIG. 31 is an exploded top perspective view of the sleeve holder of the first embodiment.
Figure 32:
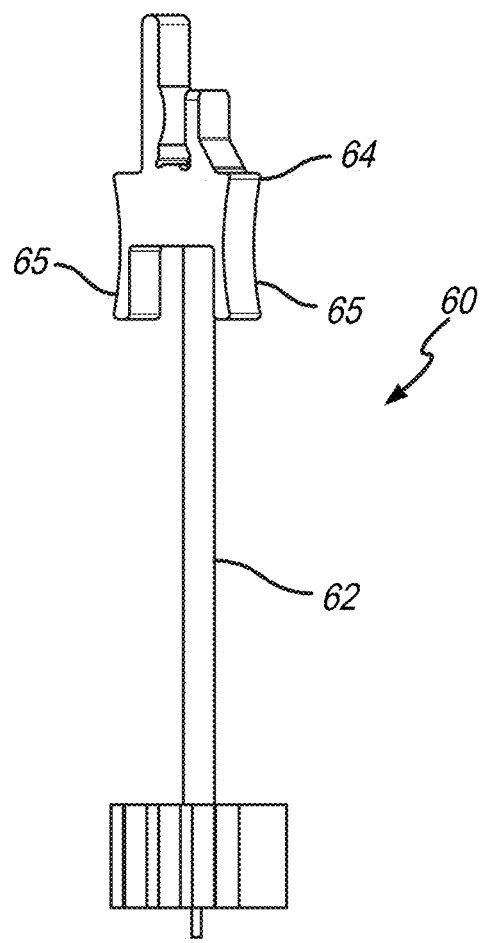
FIG. 32 is a side view of the sleeve holder of the second embodiment.
Figure 33:
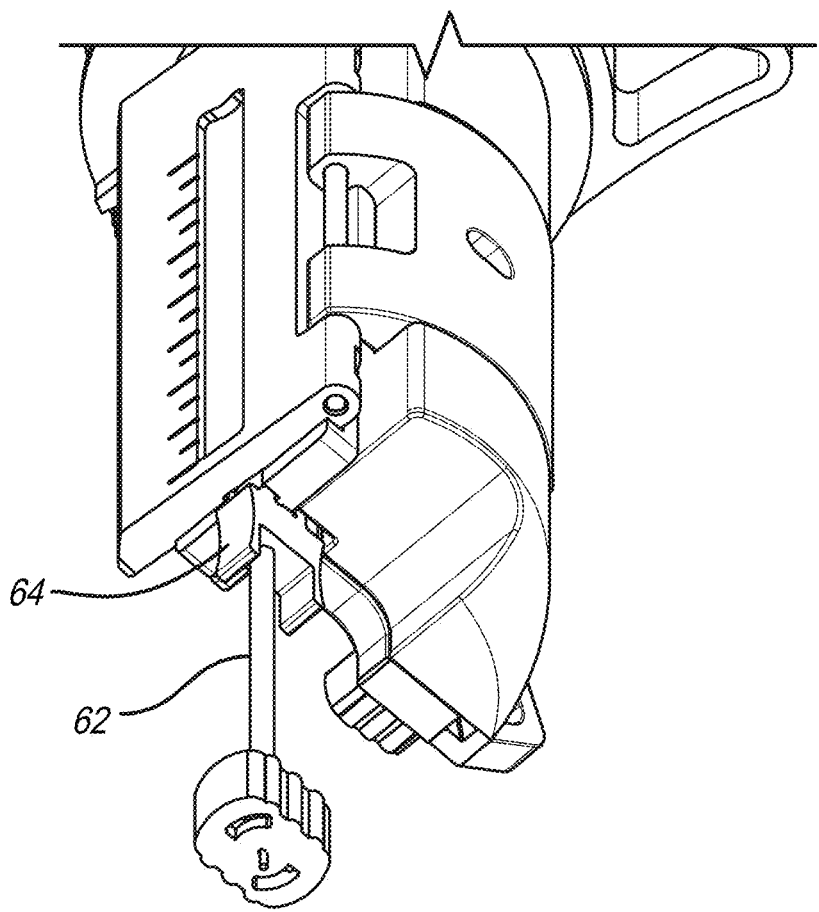
FIG. 33 is a bottom view of the second embodiment of the device with the sleeve holder connected to the inspection assembly.

A sleeve holder 60 is removably attached to the inspection assembly 40 at a mated bracket 63 that is fixed to the inspection assembly 40. In one embodiment shown in FIGS. 1 and 31, the sleeve holder 60 fits in the bracket 63 with a friction fit or snap fit. In a second embodiment shown in FIGS. 32 and 33, the head 64 of the sleeve holder 60 fits in the bracket 63 with a pinch fit. The head 64 has two arms 65 which, when pinched towards each other, release the head 64 from the bracket 63.

Figure 37:
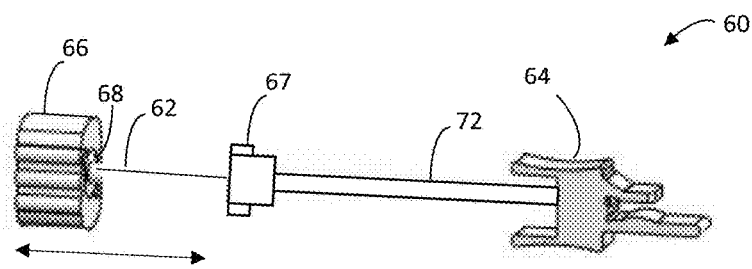
FIG. 37 is a perspective view of a sleeve holder of FIGS. 32 and 33 with a sleeve pulled partially out.
Figure 38:
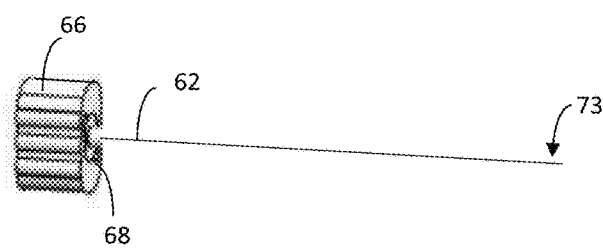
FIG. 38 is a perspective view of a sleeve pulled of the sleeve holder.
Figure 39A:
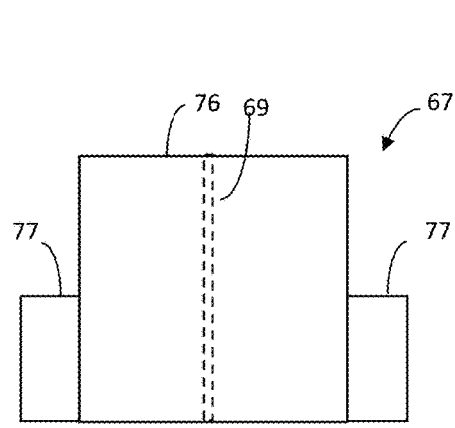
FIG. 39A is a side view of the key.
Figure 39B:
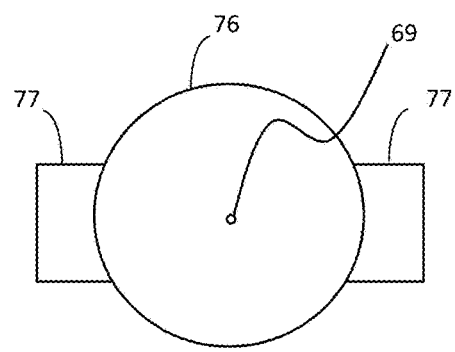
FIG. 39B is a top view of the key.
Figure 40:
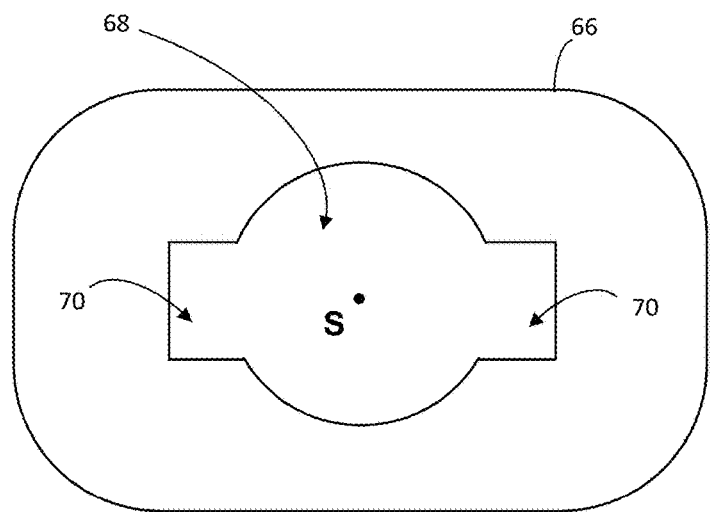
FIG. 40 is a top view of the lock.
Figure 41:
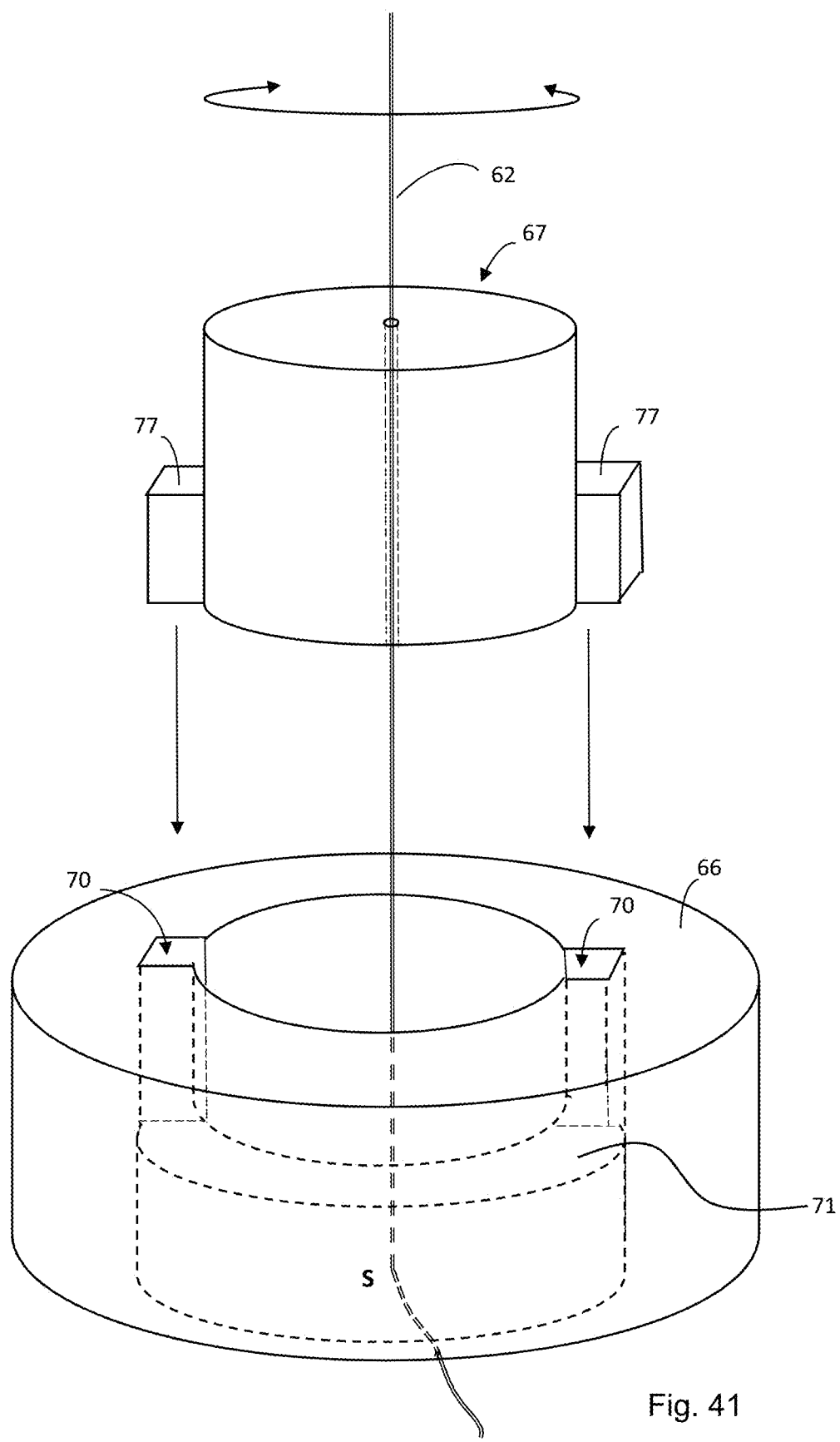
FIG. 41 is a partially-exploded view showing the key in alignment over the lock.

One end of an outer sleeve tube 72 is affixed to the head 64. See FIG. 37. The other end of the outer sleeve tube 72 is affixed to a key 67. The sleeve 62 slides within the tube 72 and is protected by it. The sleeve 62 is attached to the distal end of a lock 66, preferably irremovably, by adhesive, friction, or weld. FIGS. 40 and 41 show the attachment point S. The key 67 is mated to the lock 66. The key 67 it can be inserted into the lock 66 to secure the key 67 in the lock 66, thereby securing the sleeve 62 in the tube 72. See FIGS. 37 and 41. The sleeve 62 can be removed from the tube 72 by removing the key 67 from the lock 66 and pulling the lock 66 and connected sleeve 62 away from the tube 72.

In one embodiment, the key 67 comprises a cylindrical body 76 and tabs 77 extending therefrom. A hollow opening 69 runs through the body 76 to receive the sleeve 62. See FIGS. 37 and 39-41. The mated lock 66 is has an aperture 68 that functions as a keyhole. The aperture 68 is shaped to receive the mated key 67, permitting the tabs 77 to slide in slots 70 until the key 67 rests on the bottom of the lock 66. Then the key 67 is rotated around its longitudinal axis, until the tabs 77 are seated under the lip 71 of the keyhole 68, securing the key in the lock 66. The key 67 can be removed from the lock 66 by rotating it until the tabs are positioned under the slots and pulling the key out of the aperture 68.

Figure 36:
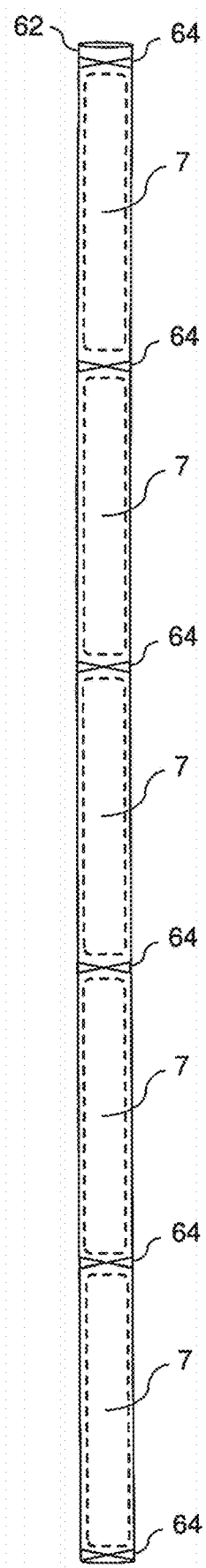
FIG. 36 is a top perspective view of a sleeve formed with pre-spaced compartments.

The lock may have knurls, texture, or other surface configurations that provide a user secure grip on the lock 66 so as to have better control over the filled sleeve while wearing surgical gloves. The sleeve holder 60 initially retains an empty sleeve 62 to receive the sequence from the inspection assembly. Optionally the sleeve 62 may be formed with pre-spaced compartments to hold each pellet in a spaced relationship with the other pellets as they are pushed into place. See FIG. 36. The compartments are separated by resilient barriers 74. Pellets are pushed into the empty sleeve and pushed past each resilient barrier by deforming it. Because the sleeve is made of a resilient material, the barrier then reforms into its original position, blocking the pellet at both ends from moving out of the compartment. Sleeves with pellets held in position with a barrier at each end permits the user to cut off a portion of the filled sleeve at the barrier without having the pellets fall out of the resultant portions of the sleeve. This in turn permits the user to modify the treatment plan quickly by trimming away unwanted pellets, without having to prepare additional filled sleeves or rearrange pellets.

In one embodiment, the resilient barriers 74 are created in the sleeve 62 punching the strand with a sharp needle at about a 45 degree angle relative to the surface of the sleeve. The angled approach is used to make it easier for the needle to penetrate the sleeve without crushing it and to give the proper angle of the burrs to hold the seeds and spacers in the sleeve when they are inserted into the strand by the strand-pusher assembly. As the sleeve is pierced, a burr is created that hangs inside the sleeve 62. This sleeve material that hangs inward acts as a resilient barrier inside the sleeve, which holds the seeds and spacers in place without using any adhesive or heat to seal the sleeve. In another embodiment, the sleeve is pinched or swaged to form the resilient barrier 74. In one embodiment, the sleeve 62 is pierced with a sharp needle to create a series of openings of about 0.20 mm each. These perforations are spaced uniformly on one side of the sleeve at about 1.5 mm and a second of perforations are formed on the opposite side of the sleeve also spaced at about 1.5 mm. See FIG. 20 (not to scale).

The sequence of seeds and spacers within each strand is defined by the needle loading plan for the patient. The sleeves are used to orient, hold, carry, and maintain spacing of the pellets to facilitate introduction into the body during brachytherapy procedures. In a preferred embodiment, a sleeve is made of a material that is compatible with ethylene oxide sterilization, non-reactive, biocompatible, and bioabsorbable within approximately 50 days post-implant. One such sleeve is made of 5/95 PLA/PGA Copolymer, [poly(lactide)/poly(glycolide)], available commercially under the trademark Max-Prene®. Sleeves are supplied non-sterile from the vendor. The sleeves are temperature and moisture sensitive. To prevent degradation of the sleeve in pouches or other containers that are opened for sampling, the remaining sleeve from a sampled container must be stored with a suitable desiccant in a properly labeled, sealed, container.

The sleeves have inside and outside diameters that are compatible with brachytherapy seeds, seed spacers and brachytherapy needles. In one embodiment a sleeve has a nominal inside diameter of 0.034 inch, a nominal outside diameter of 0.038 inch, and a nominal length of 4.7 inches. It may be necessary to cut the sleeve in order to perform required testing or placement.

To cut the filled sleeve to the desired length, the filled sleeve is first pulled out of the tube 72 by pulling the lock 66 away from the sleeve holder 60, which pulls the filled sleeve out of the tube 72. The filled sleeve is then cut to the desired length by cutting the sleeve 62 from the lock 66 at the proper location along the sleeve. The sleeve inlet end 73 may also be trimmed.

Figure 42:
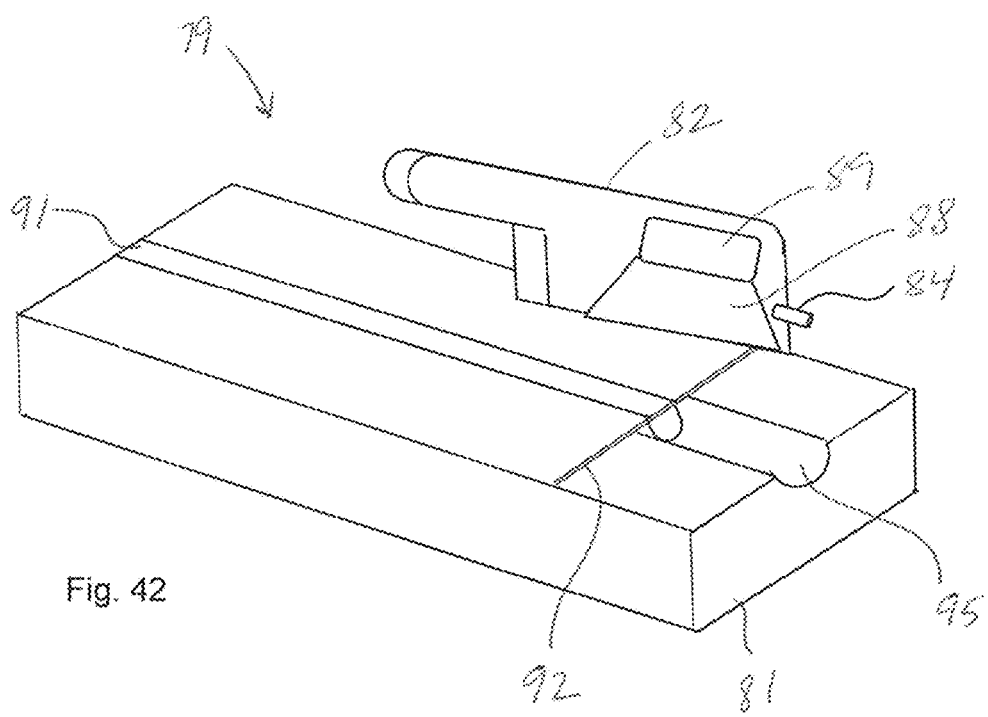
FIG. 42 is a perspective view of the cutter.

In the preferred embodiment, the filled sleeve 62 is cut to the desired length using a cutter 79 comprising a cutter base 81 and a moveable blade 88. See FIG. 42. The blade 88 can slice the sleeve 62 in a sliding motion parallel to and across the cutter base 81 or, as in the preferred embodiment, with a chopping, guillotine-type motion from above the cutter base 81. FIG. 42 shows a rotating blade arm 82 that is attached to the cutter base 81 at a pivot rod 84 and rotated from above the sleeve to be received in a blade-receiving groove 92. In a preferred embodiment, the blade-receiving groove is 0.020" wide and 0.060" deep. The blade-receiving groove 92 permits the blade 88 to move past the edge of the sleeve resting in the sleeve groove to ensure the sleeve 62 is cut all the way through.

The blade 88 is removable and replaceable. FIG. 42 shows the cutter 79 with a blade 88 attached to a blade arm 82 with a clamp 89. The blade 88 may be attached to the blade arm 82 by other fastening means, including screws or magnets, or the blade 88 may be integral with the blade arm 82. Preferably the blade 88 or the blade arm 82, or both, are disposable.

Figure 43:
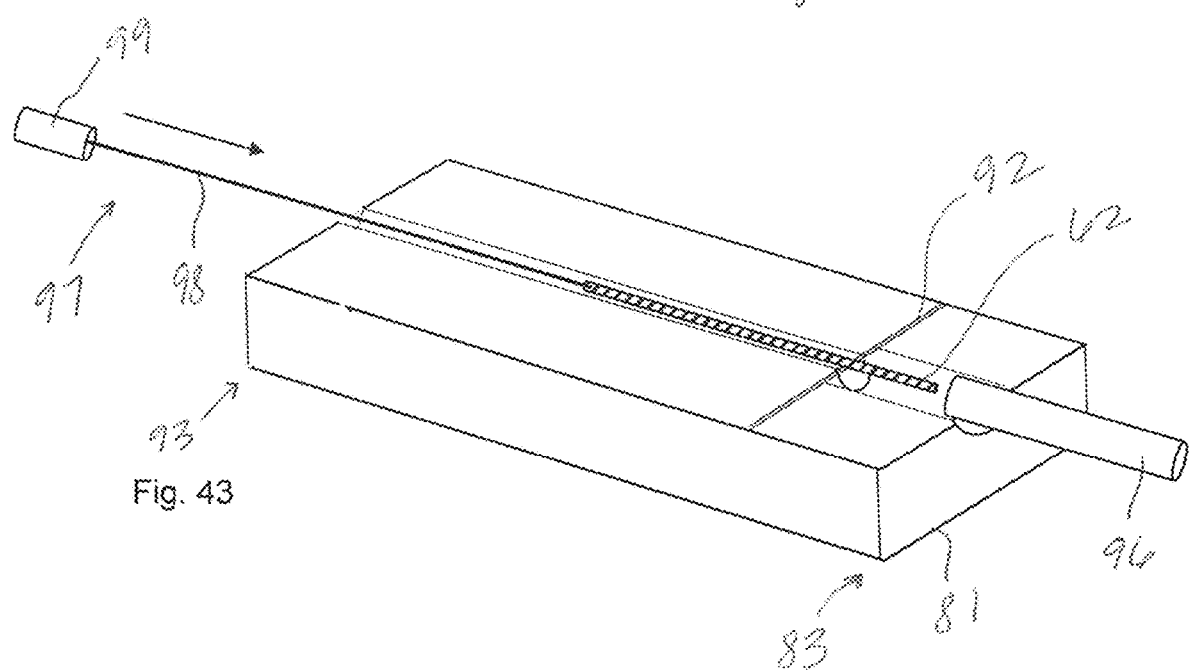
FIG. 43 is a perspective view of the cutter base and a trimmed sleeve.
Figure 44:
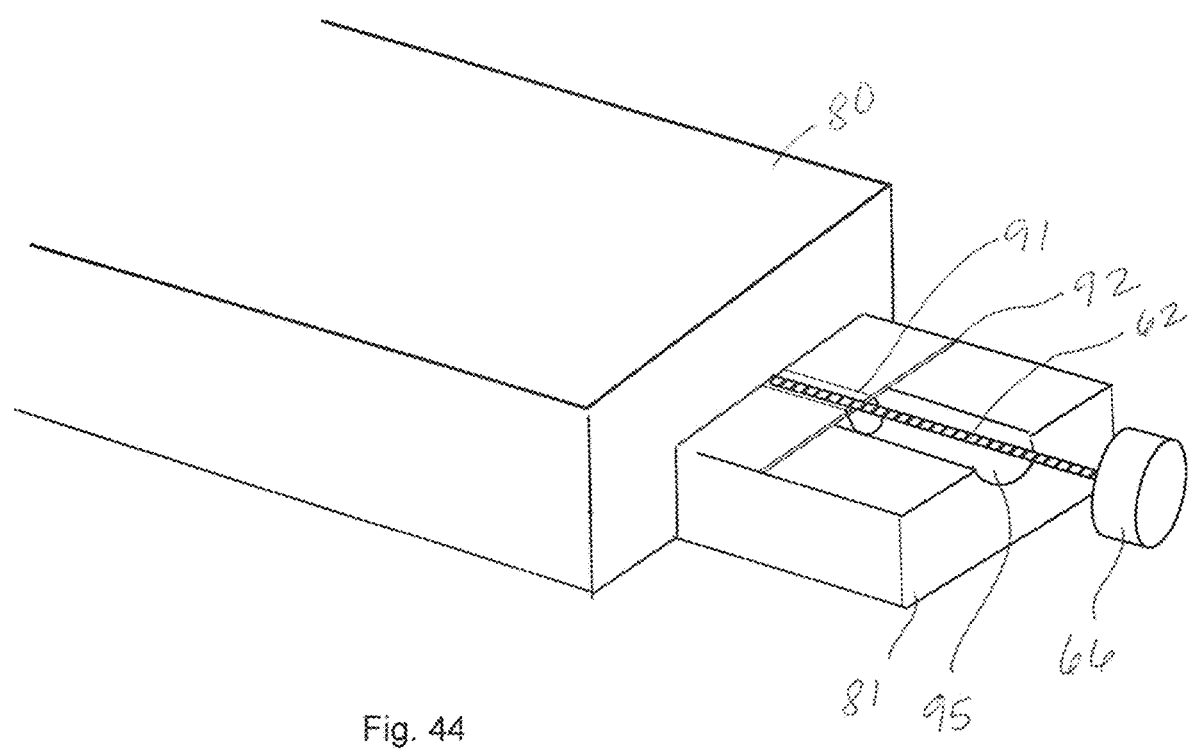
FIG. 44 is a perspective view of the cutter base with the radiation shield.
Figure 45:
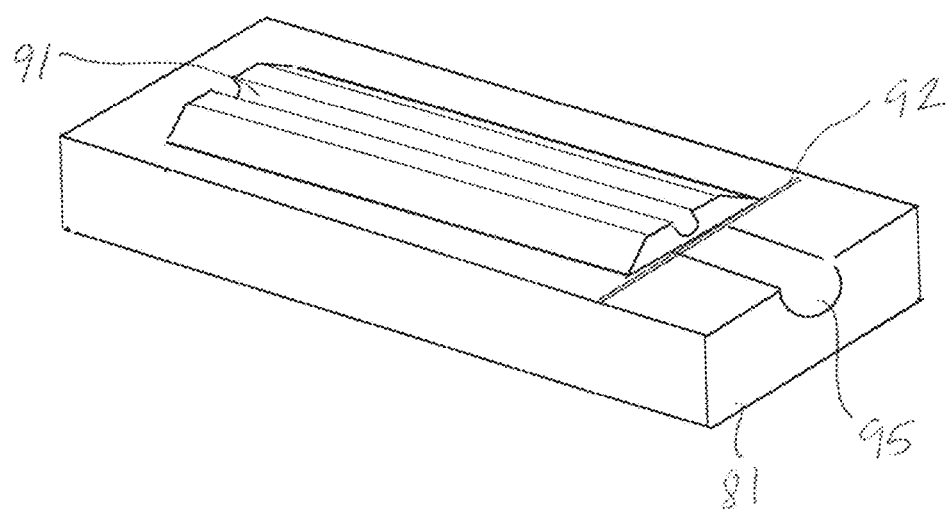
FIG. 45 is a perspective view of the cutter base with a groove in a berm.

Once the lock 66 and filled sleeve 32 have been removed from the sleeve holder 60, the filled sleeve 62 is placed in a sleeve groove 91 on a cutter base 81 with the lock 66 suspended over the blade end 83 of the cutter base. In a preferred embodiment, the sleeve groove is 0.041" wide and 0.041" deep. A radiation shield 80 is placed over the sleeve 62 and cutter base 81 while it is being cut to shield the user from the radiation emitted from the seeds. See FIG. 44. The shield 80 is made of a radio-opaque materials such as leaded-glass, which is visually transparent or translucent. The shield 80 also serves to secure the sleeve 62 in the sleeve groove 91 for cutting. The shield is preferably shaped and sized to easily be held by a gloved hand. The shield 80 may be connected to the cutter base 81 but is removable or, preferably, not connected to the cutter base 81 so that it can be removed completely for visualization, storage, and sterilization. In the event of it discoloring or cracking from repeated sterilization it can be easily replaced. The sleeve groove 91 is perpendicular to the blade-receiving groove 92 to ensure the end of the sleeve 62 is cut at a right angle to the length of the sleeve. The sleeve groove 91 may be recessed below the surface of the cutter base 81, as shown in FIGS. 42-44, or elevated above the surface of the cutter base 81, as shown in FIG. 45.

With the sleeve 62 at rest in the sleeve groove 91, the blade arm 82 is rotated down to cut the filled sleeve into two pieces at a desired location to achieve a desired sleeve length. Preferably the sleeve is sliced through a spacer to better allow a clean cut of the sleeve. Cutting the sleeve at an empty portion could collapse the empty end of the sleeve, and result in the sleeve not deploying accurately. Cutting the spacer ensures the geometry of the sleeve when cut, to allow a better deposition of the sleeve through the needle. Slicing the sleeve sliced through a spacer has the added benefit of preventing the accidental cutting of a seed. The cut also slices the lock 66 off from the sleeve 62 and the lock 66 and connected surplus sleeve are removed from the cutter base.

Once the sleeve has been cut, the blade 88 rests in the blade-receiving groove 92, blocking the end of the filled sleeve 62. The open end of a needle or a relay device 96 is placed into a needle-receiving groove 95, which is preferably co-axial with the sleeve groove so that the end of the sleeve 62 is centered in the relay device 96. In a preferred embodiment, the needle-receiving groove is 0.080" wide and 0.180" deep. The blade arm 82 is lifted and the filled sleeve 62 is pushed, using a pusher rod 97, from the pusher end 93 of the cutter base 81 towards the blade end 83 into the needle 96. The shield 80 also serves to secure the sleeve 62 in the sleeve groove 91 while it is being pushed out. See FIG. 42. The pusher rod 97 is a wire 98 or rod having a diameter that is at least as big as the diameter of the filled sleeve. The pusher rod 97 may have a cap 99 to give the user a better grip on the wire 98. The cutter base 81 have also has a place to store and secure the pusher rod 97 that can be used to advance the sleeve (while under the glass) to the proper cutting position.

The loading device is preferably made of a material that is disposable after a single use. Other embodiment employ re-usable, sterilizable materials having a suitable thickness to shield an operator from radiation emitted by radioactive seeds contained within it. Alternatively, the loading device may be reusable with some disposable parts.

Figure 35:
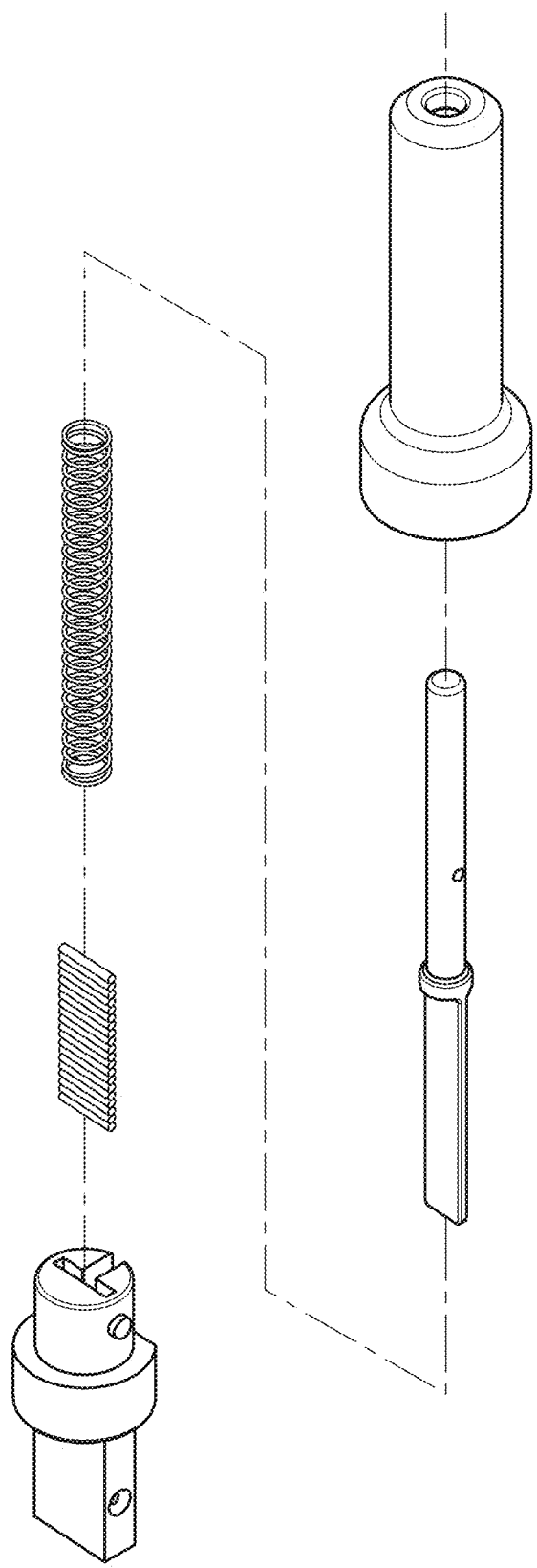
FIG. 35 is an exploded view of a Mick® cartridge of the prior art with a cover of the present invention.

A spring-biased cartridge plunger within the Mick® cartridge biases the pellets forward so that, as one pellet is pushed out, the next pellet is advanced toward the exit hole. Some Mick® cartridges 9 carry radioactive seeds, and some Mick® cartridges 9 carry spacers made of biodegradable material such as wax. The spacers tend to deform and melt together when under a load or passed through high-temperature sterilization. To prevent the spacers in the cartridge from damage during storage and transport, this invention uses a wire insert comprising a plunger pin 92 and a key pin 93 which cooperate to protect the spacers by relieving the pressure on the spacers from the spring bias. See FIG. 35. While the wire insert is in place around the cartridge, the plunger pin 92 retracts the Mick® cartridge plunger from of the stack of spacers. However, without the force on the spacers, they tend to fall out of the exit hole. The key pin 93 blocks the exit hole. The plunger pin 92 and a key pin 93 are removed from the cartridge prior to installing the spacer cartridge into the loader.

While there has been illustrated and described what is at present considered to be the preferred embodiments of the present invention, it will be understood by those skilled in the art that various changes and modifications may be made and equivalents may be substituted for elements thereof without departing from the true scope of the invention. Therefore, it is intended that this invention not be limited to the particular embodiments disclosed, but that the invention includes all embodiments falling within the scope of the appended claims.

The invention claimed is:

1. A device for cutting a brachytherapy sleeve containing pellets, the device comprising:
   a. a cutter base having a sleeve groove to receive the sleeve; and
   b. a moveable blade attached to the cutter base wherein the blade moves perpendicularly to the sleeve groove.

2. The device of claim 1 wherein the sleeve groove is elevated above the cutter base.

3. The device of claim 1 wherein the sleeve groove is recessed in the cutter base.

4. The device of claim 1 further comprising a blade-receiving groove in the cutter base to receive the blade, wherein the blade-receiving groove is perpendicular to the sleeve groove.

5. The device of claim 1 further comprising a needle-receiving groove in the cutter base, wherein the needle-receiving groove is co-axial with the sleeve groove.

6. The device of claim 1 wherein the movable blade is configured to cut the sleeve with a chopping motion from above the cutter base.

7. The device of claim 1 wherein the movable blade is configured to cut the sleeve with a sliding motion parallel to the cutter base.

8. The device of claim 1 wherein when the blade is seated in the blade-receiving groove after cutting the sleeve, the blade blocks the end of the sleeve that abuts the blade.

9. The device of claim 1 further comprising a radiation shield that mates with the cutter base to cover the sleeve groove.

10. A device for cutting a brachytherapy sleeve containing pellets, the device comprising:
    a. a cutter base having a sleeve groove to receive the sleeve; and
    b. a moveable blade arm connected to the cutter base so that the movable blade arm moves toward the sleeve from above the cutter base.

11. The device of claim 10 wherein the sleeve groove is elevated above the cutter base.

12. The device of claim 10 wherein the sleeve groove is recessed in the cutter base.

13. The device of claim 10 further comprising a blade fastened to the blade arm by a blade fastener.

14. The device of claim 10 wherein the movable blade arm is rotatably attached to the cutter base at a pivot point.

15. The device of claim 10 further comprising a needle-receiving groove in the cutter base, wherein the needle-receiving groove is co-axial with the sleeve groove.

16. The device of claim 10 further comprising a radiation shield that mates with the cutter base to cover the sleeve groove.

17. A device for cutting a brachytherapy sleeve containing pellets, the device comprising:
    a. a cutter base comprising:
       i. a sleeve groove;
       ii. a blade-receiving groove perpendicular to the sleeve groove;
       iii. a needle-receiving groove perpendicular to the blade-receiving groove;
    b. a blade arm rotatably connected to the cutter base, the blade arm comprising a blade removably fastened to the blade arm by a blade fastener;
       wherein when the blade arm is rotated towards the cutter base until the blade is seated in the blade-receiving groove thereby cutting the sleeve and blocking the end of the sleeve abutting the blade;
    c. a relay device in the needle-receiving groove; and
    d. a pusher rod configured to push the sleeve into the relay device once the blade arm is rotated away from the cutter base to remove the blade from the blade-receiving groove.

18. The device of claim 17 wherein the sleeve groove is elevated above the cutter base.

19. The device of claim 17 wherein the sleeve groove is recessed in the cutter base.

20. The device of claim 17 further comprising a radiation shield that mates with the cutter base to cover the sleeve groove.

* * * * *